(12) United States Patent
Huang

(10) Patent No.: US 12,149,034 B2
(45) Date of Patent: Nov. 19, 2024

(54) WEARABLE DEVICE FOR SENSING MOTION PARAMETER OF USER HAVING MOTION

(71) Applicant: J-MEX Inc., Hsinchu (TW)

(72) Inventor: Chun-Yuan Huang, Hsinchu (TW)

( * ) Notice: Subject to any disclaimer, the term of this patent is extended or adjusted under 35 U.S.C. 154(b) by 630 days.

(21) Appl. No.: 17/318,172

(22) Filed: May 12, 2021

(65) Prior Publication Data
US 2021/0296834 A1    Sep. 23, 2021

Related U.S. Application Data

(63) Continuation-in-part of application No. 16/825,166, filed on Mar. 20, 2020.

(30) Foreign Application Priority Data

May 13, 2020   (TW) .................................. 109115927

(51) Int. Cl.
| | |
|---|---|
| A61B 5/11 | (2006.01) |
| A61B 5/00 | (2006.01) |
| A61B 5/27 | (2021.01) |
| A61H 1/02 | (2006.01) |
| B25J 9/00 | (2006.01) |
| H01R 33/92 | (2006.01) |

(52) U.S. Cl.
CPC ................ *H01R 33/92* (2013.01); *A61B 5/11* (2013.01); *A61B 5/27* (2021.01); *A61B 5/6804* (2013.01); *A61H 1/0274* (2013.01); *B25J 9/0006* (2013.01); *A61H 2201/01* (2013.01)

(58) Field of Classification Search
CPC ................................... A61B 5/11; A61B 5/27
See application file for complete search history.

(56) References Cited

U.S. PATENT DOCUMENTS

| | | | | |
|---|---|---|---|---|
| 6,991,496 | B2 * | 1/2006 | Kuribayashi | H01R 4/242 |
| | | | | 439/404 |
| 7,164,262 | B2 * | 1/2007 | Zacay | G01D 11/24 |
| | | | | 374/E1.004 |
| 7,641,516 | B1 * | 1/2010 | Scott | H01R 13/7197 |
| | | | | 439/700 |
| 8,376,759 | B2 * | 2/2013 | Debock | H01R 12/775 |
| | | | | 439/37 |
| 9,722,375 | B2 * | 8/2017 | Chang | H01R 31/005 |
| 11,121,515 | B2 * | 9/2021 | Chahine | H01R 13/5202 |

(Continued)

*Primary Examiner* — Neil Abrams

(57) ABSTRACT

The wearable device for sensing a motion parameter of a user includes a first protection cover, a module connector, a wire connecting member, a circuit board and a plurality of spring connectors. The wire connecting member has a plurality of first electrical contacts. The first protection cover is connected to the module connector. The circuit board has a plurality of second electrical contacts corresponding to the plurality of first electrical contacts. The plurality of spring connectors are electrically connected to the plurality of first electrical contacts and the plurality of second electrical contacts correspondingly to form a plurality of first electrical connections and a plurality of second electrical connections respectively, and are configured between the module connector and the circuit board to form a plurality of first pre-deformations.

20 Claims, 18 Drawing Sheets

(56) References Cited

U.S. PATENT DOCUMENTS

| | | | |
|---|---|---|---|
| 2013/0079668 A1* | 3/2013 | Stein | A61B 5/4585 600/587 |
| 2015/0257679 A1* | 9/2015 | Ross | G01L 5/0052 702/44 |
| 2017/0319132 A1 | 11/2017 | Longinotti-Buitoni et al. | |
| 2021/0135416 A1* | 5/2021 | Huang | A61B 5/1114 |
| 2021/0296834 A1* | 9/2021 | Huang | B25J 9/0006 |

* cited by examiner

WEARABLE DEVICE FOR SENSING MOTION PARAMETER OF USER HAVING MOTION

CROSS REFERENCE TO RELATED APPLICATION

This application is a continuation-in-part of U.S. patent application Ser. No. 16/825,166, filed on Mar. 20, 2020, and claims the benefit of Taiwan's Patent Application No. 109115927, filed on May 13, 2020, at Taiwan's Intellectual Property Office, the disclosures of which are incorporated herein in their entirety by reference.

TECHNICAL FIELD

Embodiments of the present disclosure are related to a bonding device, a bonding structure, a signal connecting line, and a node device for a wearable device, and more particularly, are related to a sensing module and a signal processing module for a bonding device, a bonding structure, a signal connecting line, and a node device of the wearable device thereof.

BACKGROUND

Due to various developments in communication technology, a high-speed signal transmission scheme with low latency can enable various electronic devices to communicate with each other, and the electronic devices can transfer data to the cloud server for processing. That is, the Internet of Things (IoT) can be implemented. By means of machine learning, deep learning and big data analysis, the cloud server can analyze these data, make decisions by using artificial intelligence (AI) and even predict the occurrence of events. In the fields of health, medical rehabilitation, elderly care, entertainment, virtual reality, etc., various sensors can be used to generate various physiological or motion data on the human body to monitor the state of the human body in real time, and transmit the data to the cloud server for analysis in order to monitor an individual's health, medical treatment and care, or to achieve the efficacies of preventive medicine and health care. The physiological data or exercise data generated by these sensors can also be used in various virtual realities.

The motion state of the human body can be detected by locating motion sensors on the limbs and the trunk. A costume worn on the user, having motion sensors attached thereon is a convenient way to locate the motion sensors on the human body. In general, the sensors on the costume, the wearable device, are wired to transmit the sensing signals resulting from sensors sensing the human body motion including joints bending, limbs stretching or contracting. The wires connected to the sensors must be flexible to adapt to the body in motion and connected firmly to the sensor attached on the costume put on the body to transmit the sensed physiological signal for processing. However, in some prior-art wearable devices or equipment, the sensor is connected through the general-purpose electric wires without much flexibility to accommodate the limb in motion. Though the prior art, the published patent application with No. US20170319132, disclosed a physiological monitoring method adopting wavy wires sewn on the garment to transmit the signal of the sensor thereon, the prior art does not disclose a structure or a device to accommodate the wavy wires in an integration configuration comprising a mechanical bonding and an electrical bonding to make the wires respond to the body or limbs in motion with flexibility and transmit the signal reliably.

However, in the present invention, a configuration that integrates signal wires, motion sensors, processing modules and fabrics is disclosed, the motion sensors and the processing modules are connected to each other via the wavy signal wires embedded in the fabric to form a suite of wearable devices, and the costume, which can be worn on different limbs or trunk of the user's body for body motion sensing.

SUMMARY OF INVENTION

In view of the drawback in the above-mentioned prior art, the present invention proposes a bonding structure, a structural object or a bonding device for forming a suite of wearable devices, which includes a first bonding structure having a first signal connecting line and a second bonding structure having a second signal connecting line. The first and the second bonding structures are configured to form a combination structure, the structural object or the bonding device. Each of the first and the second bonding structures has a plurality of corresponding mechanical structures and a plurality of electrical contacts to form a mechanical bonding and an electrical bonding. The first bonding structure includes a first rigid unit having a sensing module, a first pivot connecting member and a first bonding member; and the first rigid unit is configured to form a first mechanical bonding by using a plurality of corresponding first mechanical structures, and to form a first electrical bonding by using a plurality of corresponding first electrical contacts. The second bonding structure includes a second rigid unit having a processing module, a second pivot connecting member and a second bonding member; and the second rigid unit is configured to form a second mechanical bonding by using a plurality of corresponding second mechanical structures, and to form a second electrical bonding by using a plurality of corresponding second electrical contacts.

Each of the pivot connecting members may be a wire connecting member, which may be combined with an elastic fabric and a sensing module having a plurality of flexible wires. The bonding member can be used to combine the pivot connecting member, the elastic fabric, and the sensing module to form a bonding structure for sensing the motion state of the user's limb or body. The pivot connecting member includes a plurality of connectors, each of which can be a concave or an indentation shape and includes an upper connector and a lower connector. Each of the upper and the lower connectors has a left side hole and a right side hole to bond with the bonding member mechanically. The upper connector and the lower connector may form a slot; and the plurality of flexible wires form a linear shape at its electrical connection portion where the pivot connecting member is bonded. Each of the flexible wires is embedded into each of the slots to form the electrical bonding. The upper and the lower connectors have an upper hole and a lower hole respectively, for electrically connecting the pivot connecting member with the sensing module.

The sensing module senses at least one motion parameter of the user during exercise, and then converts the at least one motion parameter into a plurality of electrical signals, where the motion parameter includes at least one of an acceleration parameter, a velocity parameter and a displacement parameter. The sensing module can transmit the plurality of electrical signals to a signal processing module for analyzing and processing by electrically connecting to the wire connecting member. The sensing module is a rigid element, and includes a protective cover, a circuit board, and a module connector. The module connector has a first tenon structure, the protective cover has a second tenon structure, and the first tenon structure is engaged with the second tenon structure to encapsulate the circuit board in the sensing module.

In order to enable the sensing module to be easily worn on different parts of the user, or to facilitate replacement or maintenance, the sensing module has a detachable structure, which is designed to have a gap between the protective cover and the module connector, so that the protective cover can be disassembled with bare hands or with appropriate tools. The circuit board is fixed to the protective cover, so the circuit board is also separated after the protective cover is separated from the module connector. The gap is designed for the disassembly and assembly of the device shell, but the gap can cause the relative displacement of the circuit board and the contact reed of the connecting wire when the human body moves, which affects the electrical transmission. Therefore, the spring connector having a pre-force to be deformable adapts to the gap change caused by human movement, and always keeps reliable electricity transmission.

A motion sensing module is provided in the present disclosure, and is formed by combining a plurality of rigid structural members, and the corresponding joints of the plurality of rigid structural members that are combined with each other have a joint gap with a variable displacement amount. A plurality of deformable joints are correspondingly arranged at the plurality of joints to join the plurality of joint members.

The module connector of the sensing module is combined with a connecting member. A wire connecting member is fixed on the connecting member, and has a plurality of first electrical contacts. The circuit board has a plurality of second electrical contacts. A plurality of spring connectors between the circuit board and the wire connecting member are used to maintain the reliability of the electrical connection. Each of the plurality of spring connectors can be a compression spring. Due to the design of the gap and the engagement of the first tenon (or locking) structure and the second tenon (or locking structure), they are not tightly closed and locked, so the gap between the protection cover of the sensing modules and the module connector worn on the body can change due to body movement when the user exercises, which easily affects the stability of the electrical connections (or bonds) between the plurality of second electrical contacts on the circuit board and the plurality of first electrical contacts of the wire connecting member. Each of the spring connectors is arranged between the circuit board and the wire connecting member. When the protective cover is joined to the module connector, a bonding device of a wearable device is formed, which is compressed and pre-deformed. After the protection cover and the module connector are engaged to form the gap, the plurality of spring connectors can expand or contract in length to support the circuit board and the wire connection member when the body moves and the gap becomes larger or smaller. This offsets the instability of the electrical connection that may occur due to the change of the gap, and ensures the reliability of the electrical connection. The signal processing module has a first structure being similar to a second structure of the sensing module; and the signal processing module can also be used with a first method being similar to a second method of the sensing module to maintain the reliability of the electrical connection.

In accordance with one embodiment of the present disclosure, a wearable device for sensing a motion parameter of a user having a motion is provided. The wearable device for sensing a motion parameter of a user having a motion includes a first bonding structure. The first bonding structure has a plurality of first electrical contacts and a plurality of second electrical contacts to form correspondingly a plurality of first electrical bonds, and includes a first module connector, a first wire connecting member, a first protection cover and a plurality of first spring connectors. The first module connector has a first tenon structure. The first wire connecting member has the plurality of first electrical contacts. The first protection cover is connected to the first module connector via the first tenon structure, wherein before the first module connector and the first protection cover is connected, a first gap is formed therebetween. The first circuit board is fixed on the protecting cover, is configured between the first module connector and the first protection cover, and has the plurality of second electrical contacts. The plurality of first spring connectors are respectively electrically connected between the plurality of first and second electrical contacts to form a plurality of first and a plurality of second electrical connections respectively, and are configured between the first module connector and the first circuit board to form a plurality of first pre-deformations, wherein when the user has the motion, the plurality of first spring connectors ensure, despite the first gap, that the pluralities of the first and second electrical contacts keep therebetween the plurality of first electrical bonds.

In accordance with another embodiment of the present disclosure, a wearable device for sensing a motion parameter of a user is provided. The wearable device for sensing a motion parameter of a user includes a module connector, a wire connecting member, a circuit board and a plurality of spring connectors. The wire connecting member has a plurality of first electrical contacts. The first protection cover connects thereto the module connector. The circuit board has a plurality of second electrical contacts corresponding to the plurality of the first electrical contacts. The plurality of spring connectors are electrically connected to the plurality of first electrical contacts and the plurality of second electrical contacts correspondingly to form a plurality of first electrical connections and a plurality of second electrical connections respectively, and are configured between the first module connector and the first circuit board to form a plurality of first pre-deformations.

In accordance with a further embodiment of the present disclosure, a wearable device for a user for sensing a motion parameter of the user is provided. The wearable device for a user for sensing a motion parameter of the user includes a device body, a plurality of wires, a circuit board and a plurality of spring connectors. The device body has plural first electrical contacts. The plurality of wires are disposed on the device body for conducting a plurality of electrical signals reflecting the motion parameter. The circuit board is disposed on the device body and has a plurality of second electrical contacts. The plurality of spring connectors are electrically connected between the plurality of second electrical contacts and the plurality of wires respectively to form a pre-stressed electrical connection therebetween.

The above embodiments and advantages of the present invention will become more readily apparent to those ordinarily skilled in the art after reviewing the following detailed descriptions and accompanying drawings:

DETAILED DESCRIPTION OF THE PREFERRED EMBODIMENTS

Please refer to all FIGS. of the present invention when reading the following detailed description, wherein all FIGS. of the present invention demonstrate different embodiments of the present invention by showing examples, and help the skilled person in the art to understand how to implement the present invention. The present examples provide sufficient embodiments to demonstrate the spirit of the present invention, each embodiment does not conflict with the others, and new embodiments can be to implemented through an arbitrary combination thereof, i.e., the present invention is not restricted to the embodiments disclosed in the present specification.

Figure 1A:
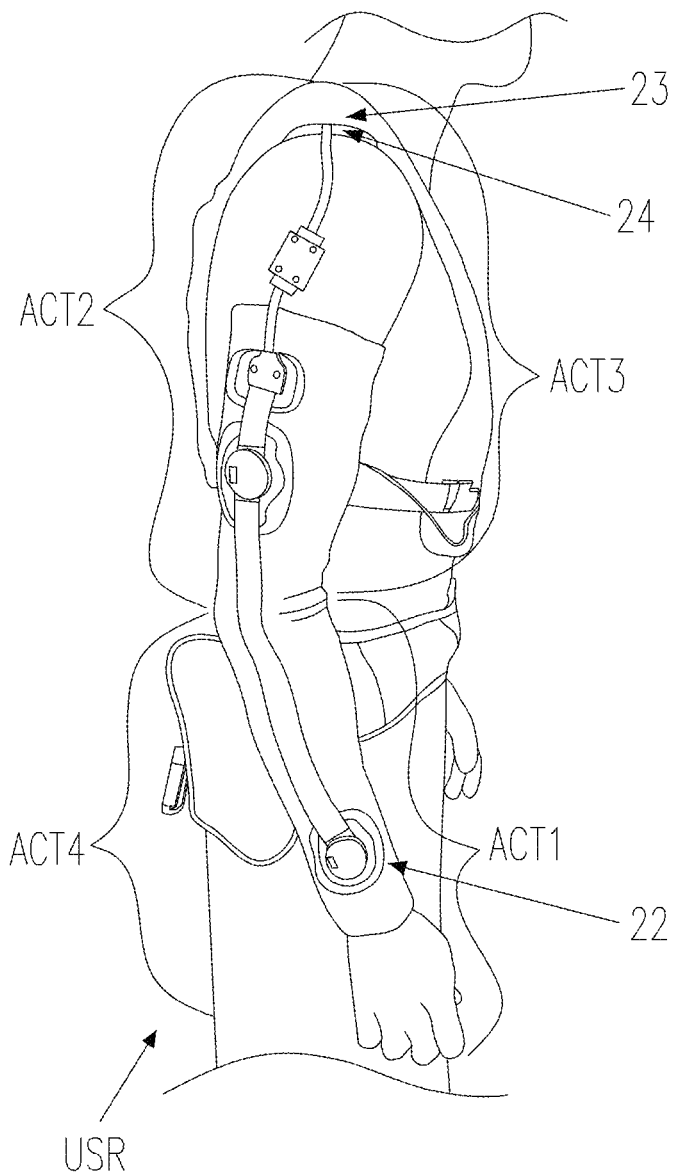
FIGS. 1A and 1B are schematic configuration diagrams showing a combined assembly of a wearable device on the limbs according to a preferred embodiment of the present disclosure.
Figure 1B:
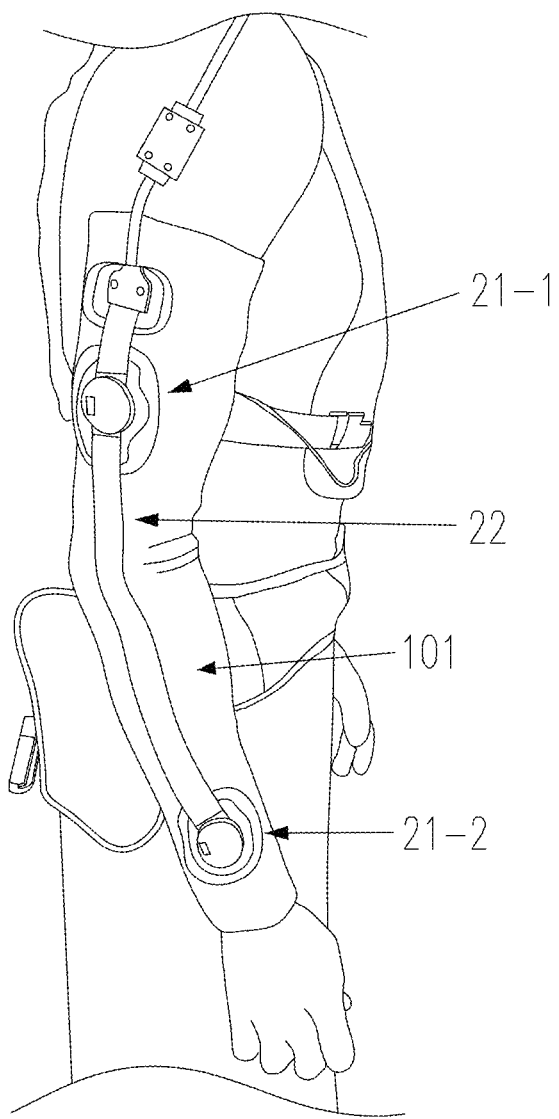
Figure 2:
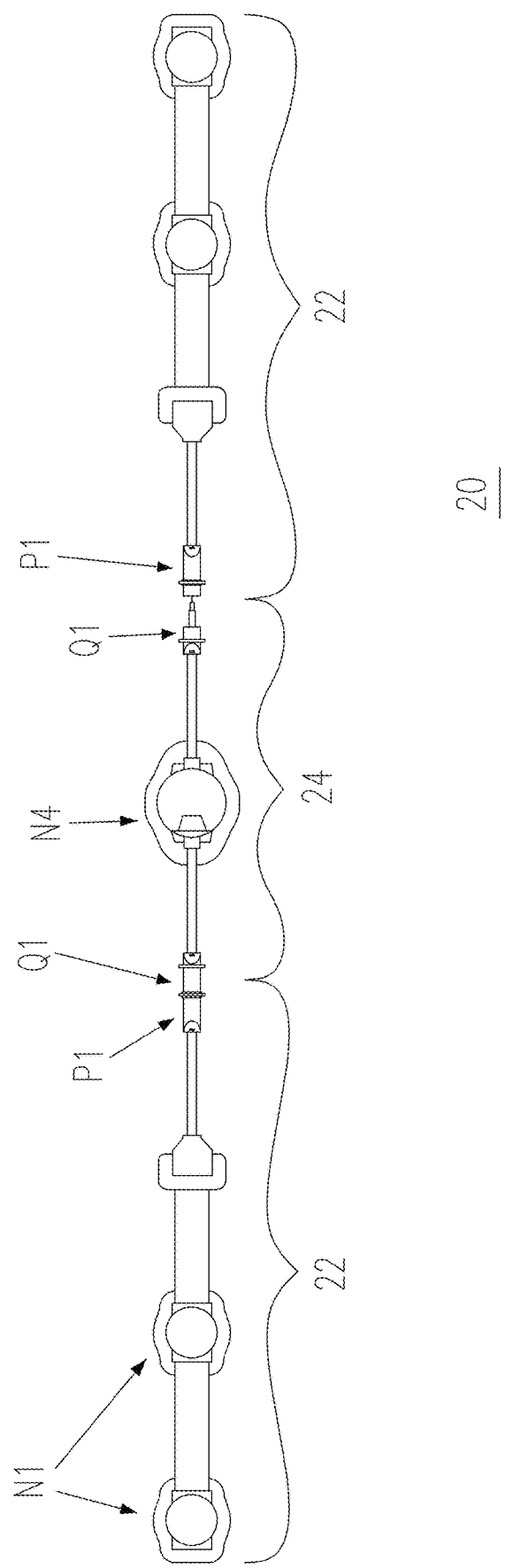
FIG. 2 is a schematic diagram showing bonding devices of a wearable device according to a preferred embodiment of the present disclosure.
Figure 3:
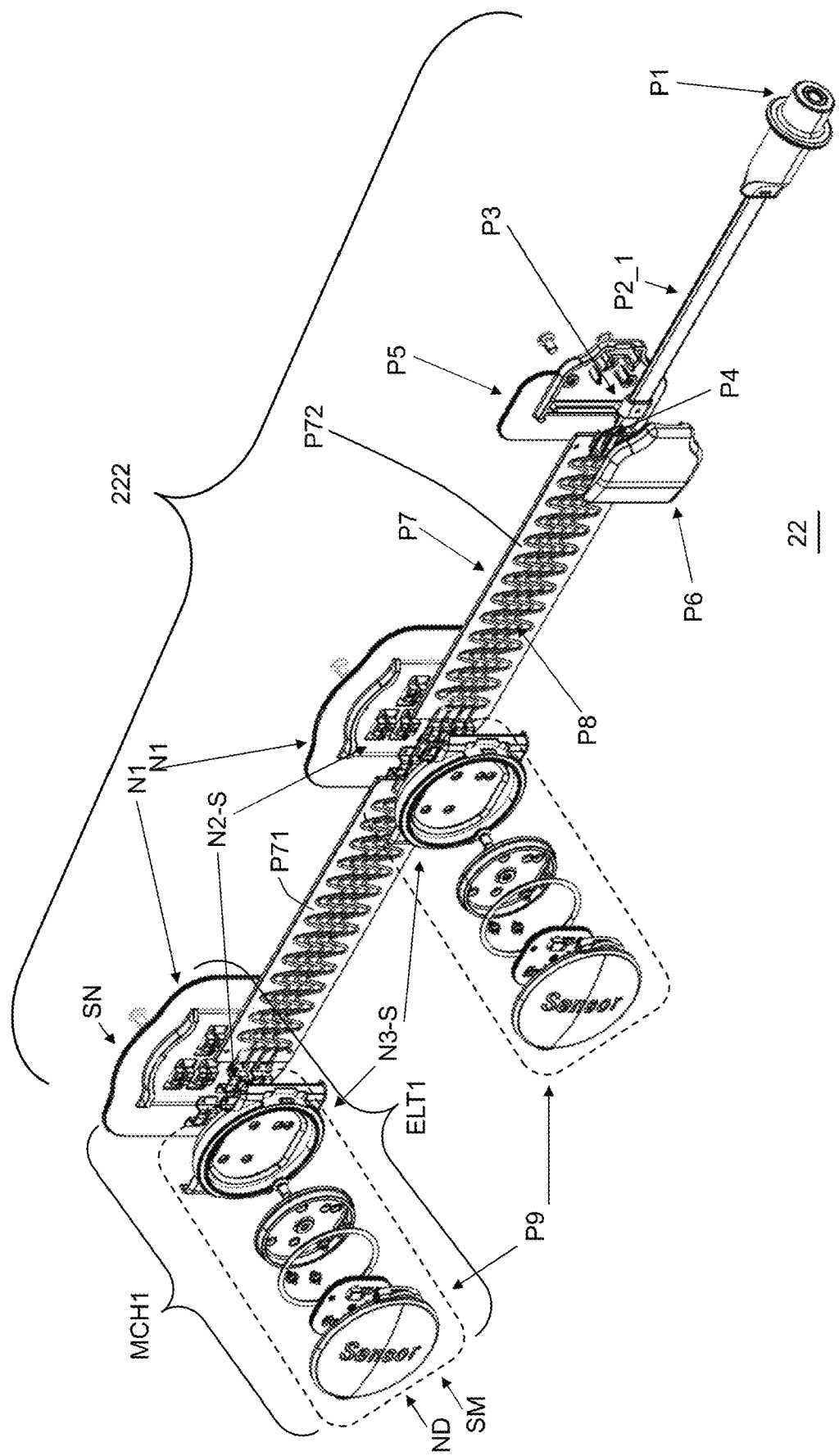
FIG. 3 is a schematic diagram showing a first bonding structure according to a preferred embodiment of the present disclosure.
Figure 4:
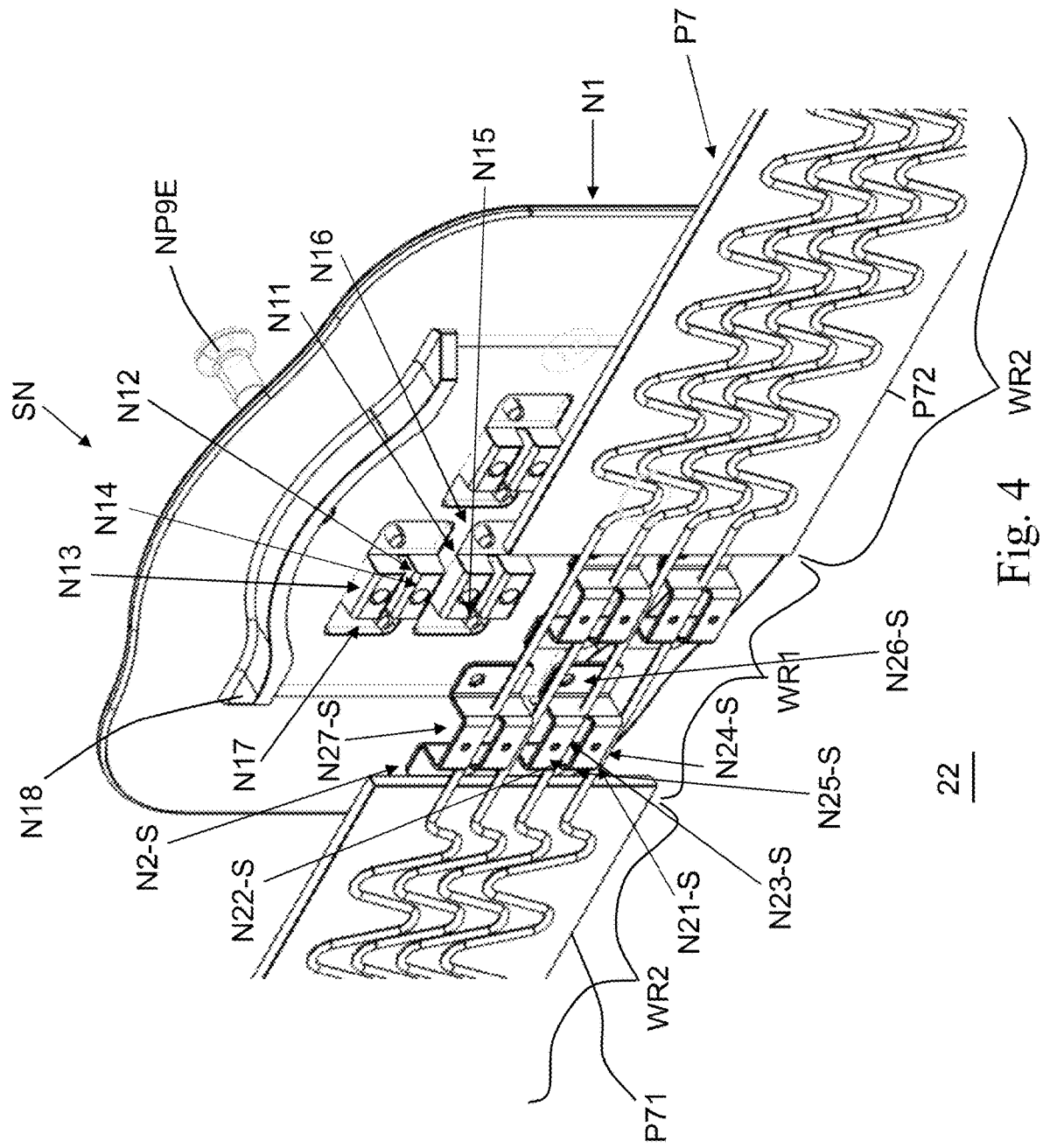
FIG. 4 is a schematic diagram showing an internal structure of the first bonding structure according to a preferred embodiment of the present disclosure.

Please refer to FIGS. 1A and 1B, which are schematic configuration diagrams showing a bonding device 10 of a wearable device on the limbs according to a preferred embodiment of the present disclosure. Please refer to FIG. 2, which is a schematic diagram showing bonding devices 22 and 24 of a wearable device 20 according to a preferred embodiment of the present disclosure. Please refer to FIG. 3, which is a schematic diagram showing a first bonding structure 22 according to a preferred embodiment of the present disclosure. Please refer to FIG. 4, which is a schematic diagram showing an internal structure of the first bonding structure 22 according to a preferred embodiment of the present disclosure. Please refer to FIGS. 1, 2, 3 and 4 for the following descriptions. The bonding device 10 for a wearable device includes a first bonding structure 22 and a second bonding structure 24 (as shown in FIG. 2). The first bonding structure 22 has corresponding plural first mechanical structures (for example, N21-S, N11, N25-S, N26-S, N15 and N16 as shown in FIG. 4) and corresponding plural first electrical contacts (for example, N23-S, N24-S, N13 and N14 as shown in FIG. 4) to form a first mechanical bond MCH1 and a first electrical bond ELT1 (as shown in FIG. 3). The first bonding structure 22 includes a first wire connecting member N2-S, a first bonding member N1 and an elastic member P7. The first wire connecting member N2-S, the first bonding member N1 and the elastic member P7 are configured to form the first mechanical bond MCH1 through corresponding plural first mechanical structures, for example, N21-S(hole), N11 (protrusion), N25-S(hole not shown), N26-S(hole), N15 (protrusion) and N16 (protrusion). The first wire connecting member N2-S, the first bonding member N1 and the elastic member P7 are configured to form the first electrical bond ELT1 through the plurality of first electrical contacts, for example, N23-S (protruding type conduction member), N24-S(protruding type conduct member), N13 (protruding type conduct connector) and N14 (protruding type conduction connector). Please refer to FIG. 5, which is a schematic diagram showing a second bonding structure 24 according to a preferred embodiment of the present invention. The second bonding structure 24 includes a first signal connecting line P2_2. The plurality of first wires P8 attached on the elastic member P7, as shown in FIG. 4, are electrically connected to the plurality of second wires P4 of the first signal connecting line P2_1 to combine the first bonding structure 22 with the second bonding structure 24.

As shown in FIGS. 1A and 1B, the first bonding structure 22 and the second bonding structure 24 are attached to the fabric 101 by the attachment members 21 (21_1 and 21_2) shown in FIGS. 1B, and 23 shown in FIG. 1A, for example, attached to the clothing of the user USR. The attachment members 21-1 and 21-2 of the first bonding structure 22 are respectively disposed on the upper arm and the lower arm of the user USR, in a non-joint position, so that sensors can detect motion status of the limbs of the user USR when the user USR exercises the limbs. In FIG. 1A, the attachment member 23 not shown, is located under the fabric on the shoulder.

In any one of the aforementioned embodiments of the present disclosure, the first wire connecting member N2-S includes a plurality of first connectors N21-S, each of which has a plurality of first mechanical contacts N25-S and N26-S and a plurality of first connecting slots N22-S. The first bonding member N1 includes a plurality of second connectors N11, each of which has a plurality of second mechanical contacts N15 and N16. For example, the plurality of first mechanical structures N21-S, N11, N25-S, N26-S, N15 and N16 include the plurality of first connectors N21-S, the plurality of second connectors N11, the plurality of first mechanical contacts N25-S and N26-S, and the plurality of second mechanical contacts N15 and N16. The elastic member P7 has a plurality of first wires P8. The plurality of first wires P8 are respectively inserted into (or embedded into or by means of soldering) the plurality of first connecting slots N22-S for electrically connecting the first wire connecting member N2-S. The plurality of first mechanical contacts N25-S and N26-S are respectively inserted into the plurality of second mechanical contacts N15 and N16, so that the plurality of first connectors N21-S are respectively inserted into the plurality of second connectors N11 for mechanically connecting the first bonding member N1. The arrangement of the plurality of first connectors N21-S may be interleaved with each other for adjacent connectors in a vertical direction.

In any one of the aforementioned embodiments of the present disclosure, the first bonding structure 22 is configured to be worn on an active portion (at least one of ACT1, ACT2, ACT3 and ACT4) of a user USR. The active portion (at least one of ACT1, ACT2, ACT3 and ACT4) includes at least one of limbs, head, neck, body and hips. The elastic member P7 is an elastic fabric member, and includes a plurality of elastic fabrics P71 and P72, as shown in FIG. 4, and a plurality of first wires P8 shown in FIG. 3, wherein the plurality of elastic fabrics P71 and P72 are attached thereon the plurality of first wires P8 respectively. Alternatively, the plurality of first wires P8 can be knitted on the plurality of elastic fabrics P71 and P72. The plurality of first wires P8 are evenly spaced, wavy, and thus flexible. Each of the plurality of first connectors N21-S is a conductor connector; and each of the plurality of second connectors N11 is an isolator. The plurality of second connectors N11 have a plurality of second connecting slots N12 respectively. The plurality of first wires P8 are respectively inserted into the plurality of first connecting slots N22-S for electrically connecting; and then the plurality of first connecting slots N22-S are arranged in the plurality of second slots N12 for mechanically connecting the first bonding member N1. The plurality of first mechanical contacts N25-S and N26-S include a plurality of via holes (for example, a left side hole N25-S and a right side hole N26-S); and the plurality of second mechanical contacts N15 and N16 include a plurality of protrusions (for example, a left protrusion N15 and a right protrusion N16) respectively inserted into the plurality of via holes for connecting with the plurality of first connectors N21-S mechanically. Each of the plurality of first connectors N21-S has a concave portion N27-S and a plurality of first electrical contacts N23-S, N24-S located at a bottom of the concave portion N27-S, each of the plurality of second connectors N11 has a protruding portion N17, an upper connector hole N13 and a lower connector hole N14 located at a top of the corresponding protruding portion N17. Each of the plurality of protruding portions N17 is inserted into the respective concave portion N27-S; and the plurality of first electrical contacts N23-S and N24-S are a pair of contacts respectively mechanically connected to the upper connector hole N13 and the lower connector hole N14, such that the plurality of first connectors N21-S and the plurality of second connectors N11 are respectively connected mechanically. In FIG. 4, the plurality of electrical contacts N23-S and N24-S are an upper hole N23-S and a lower hole N24-S of the first connector N21-S.

Figure 6:
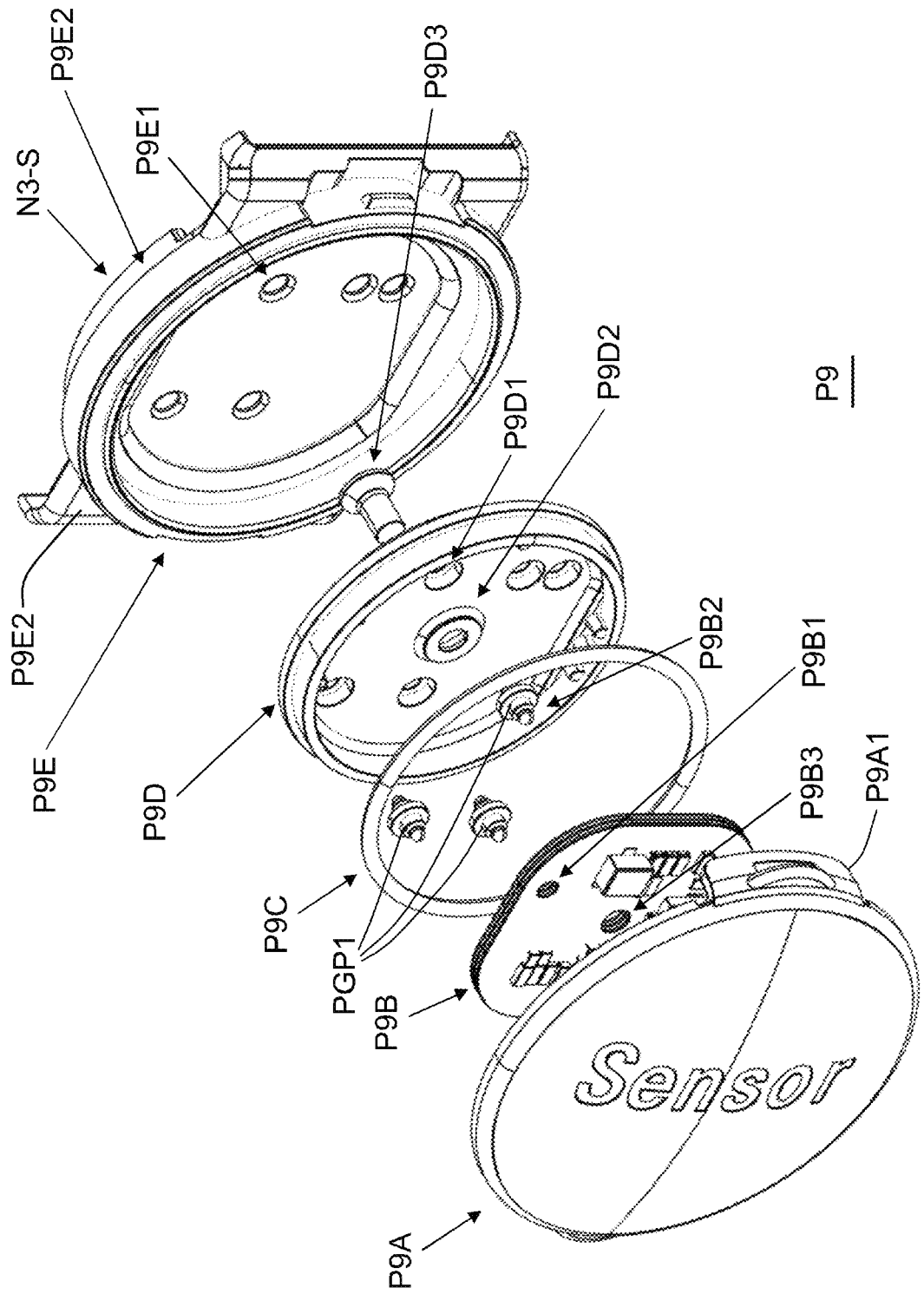
FIG. 6 is a schematic diagram showing a rigid unit according to the preferred embodiment of the present invention.

Please refer to FIG. 6, which is a schematic diagram showing a rigid unit P9 according to the preferred embodiment of the present invention. Please refer to FIG. 7, which is a schematic diagram showing electrical holes for identifying positions of a rigid unit P9 according to the preferred embodiment of the present invention. Please refer to FIGS. 6 and 7 for the following descriptions. For example, the rigid unit P9 is a motion sensing module, which includes a module connector N3-S(i.e., a module connector P9E of the rigid unit P9), a PCB (Print Circuit Board) connector P9D, an engaging ring P9C, a PCB P9B and a protection cover P9A.

Figure 7:
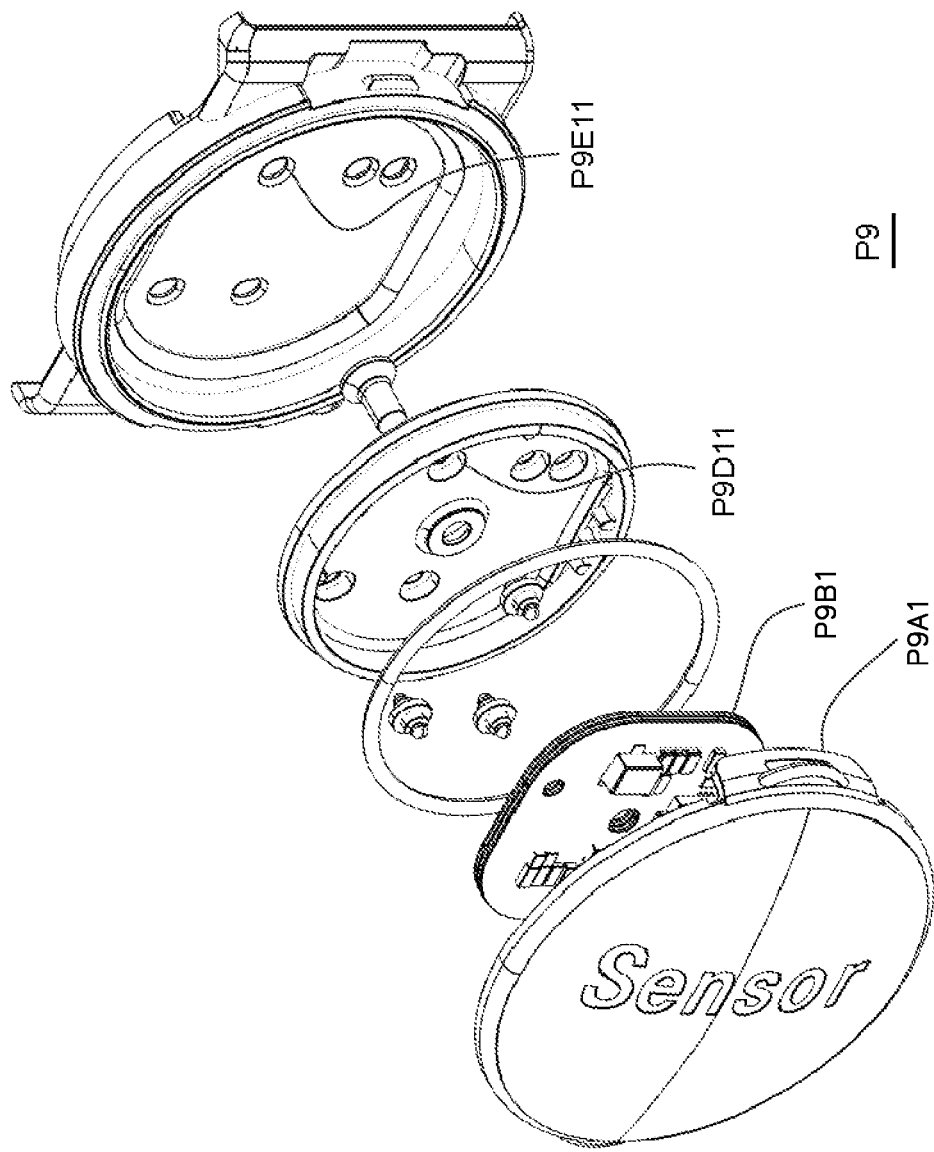
FIG. 7 is a schematic diagram showing electrical holes for identifying positions of the rigid unit according to a preferred embodiment of the present invention.

Please refer to FIGS. 4, 6 and 7. In any one of the aforementioned embodiments, the first wire connecting member N2-S includes the plurality of first electrical contacts N23-S and N24-S. The first bonding structure 22 further includes a rigid unit P9 having a plurality of second electrical contacts P9E1, P9D1, P9B2, P9B1, P9E11 and P9D11 (as shown in FIGS. 6 and 7); and the plurality of second electrical contacts P9E1, P9D1, P9B2 and P9B1 are electrically connected to the plurality of first electrical contacts N23-S and N24-S to electrically connect the rigid unit P9 to the first wire connecting member N2-S(as shown in FIGS. 4, 6 and 7). At least one of the plurality of second electrical contacts P9E1, P9D1, P9B2, P9B1, P9E11 and P9D11 (for example, P9E11 and P9D11) is used to form a conduction or a disconnection, wherein the conduction or the disconnection is used to determine a wearing position of the rigid unit P9.

In FIG. 6, the PCB P9B is fixed to the PCB base P9D through the PCB base positioning hole P9B3, the PCB base positioning hole P9D2, the PCB fixing member P9D3, and the electrical contacts P9B1 and P9D1; and the engaging ring P9C is sleeved on the PCB base P9D, and is then plugged into the module connection base N3-S, so that the PCB base P9D is fixed in the module connection base N3-S, and then the cover P9A covers the module connection base N3-S. Please refer to FIGS. 4, 6 and 7. In any one of the aforementioned embodiments, the module connection base N3-S has a curved protrusion structure P9E2, and the first bonding member N1 also has a curved like structure N18, which is used to fix the module connection base N3-S to the first bonding member N1. Each of the plurality of second connectors N11 further includes a plurality of holes N13 and N14, wherein the plurality of first electrical contacts N23-S and N24-S are respectively coupled to the plurality of holes N13 and N14 and the plurality of second electrical contacts P9E1, P9D1, P9B2, P9B1, P9E11 and P9D11, such that the rigid unit P9 is fixed to the first bonding member N1. The stabilization unit NP9E passes through the first bonding member N1 and is locked into an internal screw hole (located on the back of the module connection base N3-S, not shown) of the module connection base N3-S, so that the rigid unit P9 is directly connected with the first bonding member N1 to mechanically increase the stability of the rigid unit P9 and prevent loosening.

In FIG. 3, the first bonding structure 22 further includes a signal line fixing component P3 and a second signal connecting line P2_1. The second signal connecting line P2_1 includes a plurality of second wires P4 and a signal connecting hole P1, wherein the plurality of first wires P8 are electrically connected to the plurality of second wires P4 respectively at the signal line fixing component P3. The signal line fixing element P3 includes a protection cover P6 and a protection base P5 for fixing and packaging the plurality of second wires P4 to ensure the transmission of electrical signals. The first bonding structure 22 is combined with the second bonding structure 24 to form the bonding device 20, wherein the second bonding structure 24 includes a signal connector Q1 (as shown in FIG. 2) for electrically connecting the signal connecting hole P1.

Figure 8:
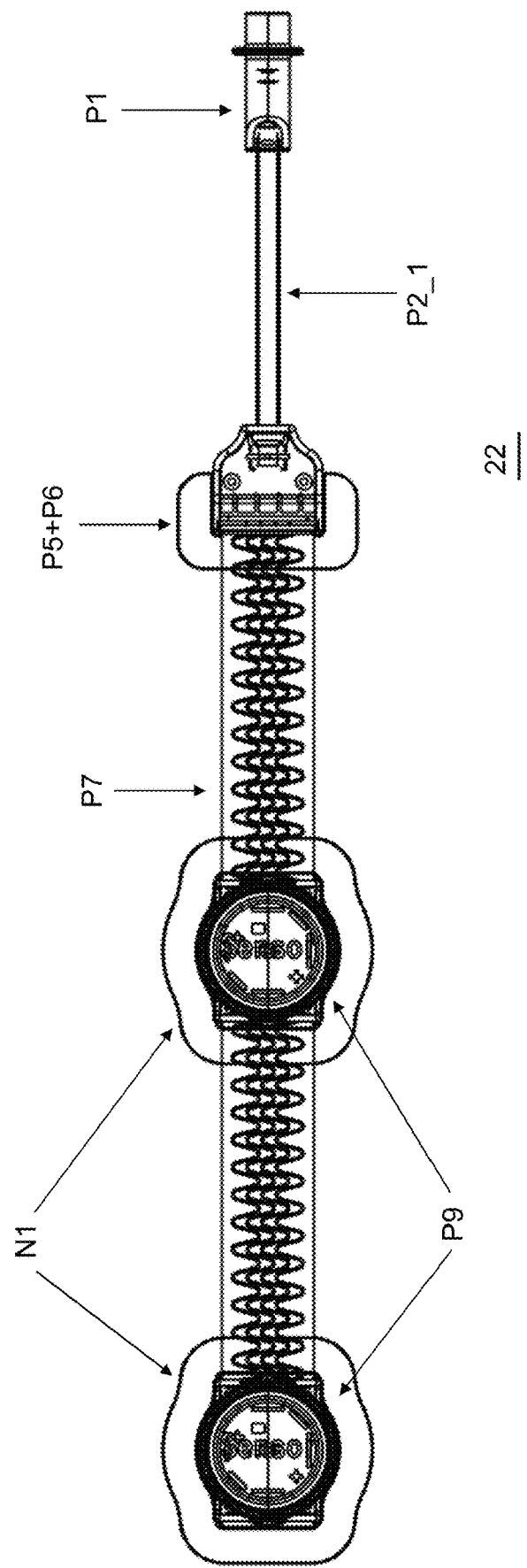
FIG. 8 is a schematic diagram showing a first bonding structure according to a preferred embodiment of the present invention.

Please refer to FIG. 8, which is a schematic diagram showing a first bonding structure 22 according to a preferred embodiment of the present invention. It can be seen in FIG. 8 that the first bonding structure 22 includes two rigid units P9 (such as a motion sensing module), each of the first bonding members N1 and each of the first wire connecting members N2-S are used to connect each of the rigid unit P9 to the flexible member P7 having a flexible plurality of first wires P8 by the mechanical bond MCH1 and the electrical bond LET1 (as shown in FIGS. 3, 4 and 8). The protection cover P6 and the protection base P5 are used to fix the plurality of flexible wires P8 and the signal connecting line P2_1. The signal sensed by the motion sensing module can be transmitted to the data collection center through the signal connecting line P2_1, and then transmitted to the back-end computing center by the data collection center for analyzing.

Figure 9:
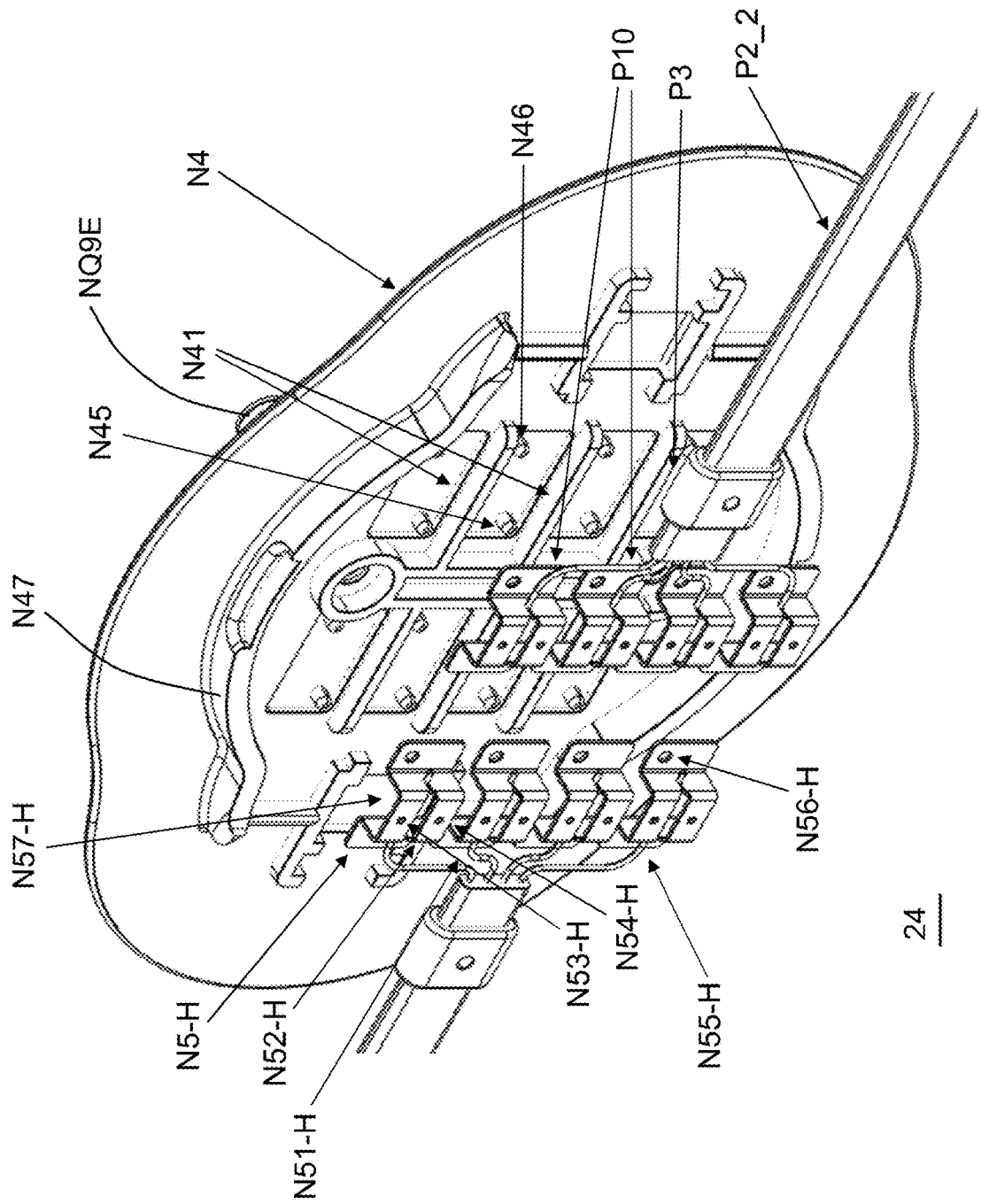
FIG. 9 is a schematic diagram showing an internal structure of a second bonding structure according to a preferred embodiment of the present invention.

Please refer to FIG. 9, which is a schematic diagram showing an internal structure of a second bonding structure 24 according to a preferred embodiment of the present invention. Please refer to FIGS. 5 and 9. The second bonding structure 24 further includes a second wire connecting member N5-H having a plurality of third connectors N51-H, each of which has a third connecting slot N52-H and a plurality of third mechanical contacts N55-H and N56-H, for example, a left side hole N55-H (hole not shown) and a right side hole N56-H of the second wire connecting member N5-H. The second bonding structure 24 further includes a second bonding member N4 including a plurality of fourth mechanical contacts N45 and N46, each of the position of which is arranged according to each of the third mechanical contacts N55-H and N56-H correspondingly, for example, a left positioning protrusion N45 and a right positioning protrusion N46 on the second bonding member N4. The signal connecting line P2_2 has a plurality of second wires P10. The plurality of third connectors N51-H have a plurality of third connecting slots N52-H respectively. The plurality of second wires P10 are inserted into (or soldered to) the plurality of third connecting slots N52-H respectively, for electrically connecting to the second wire connecting member N5-H. The plurality of third mechanical contacts N55-H and N56-H are inserted into the plurality of fourth mechanical contacts N45 and N46 correspondingly, for connecting with the second bonding member N4 mechanically. The second bonding structure 24 is detachably fitted to a relatively stable portion of a user USR, for example, the stable portion includes at least one of a shoulder, a chest, a back and a waist. The second bonding member N4 further includes a plurality of positioning protrusions N41. The plurality of third connectors N51-H are configured to mechanically connect to the second bonding member N4 according to the plurality of positioning protrusions N41; for example, each of the plurality of positioning protrusions N41 is a positioning board. Each of the plurality of third connectors N51-H is a conductor connector, and the plurality of positioning protrusions N41 are respectively a plurality of insulator portions. The plurality of third mechanical contacts N55-H and N56-H include a plurality of via holes; and the plurality of fourth mechanical contacts N45 and N46 include a plurality of fixing protrusions. The plurality of fixing protrusions respectively penetrate the plurality of via holes to mechanically connect to the plurality of third connectors N51-H. Each of the third connectors N51-H further has a recess N57-H and a plurality of first electrical contacts N53-H and N54-H located on the recess N57-H, for example, an upper hole N53-H and a lower hole N54-H of each of the third connector N51-H.

Figure 10:
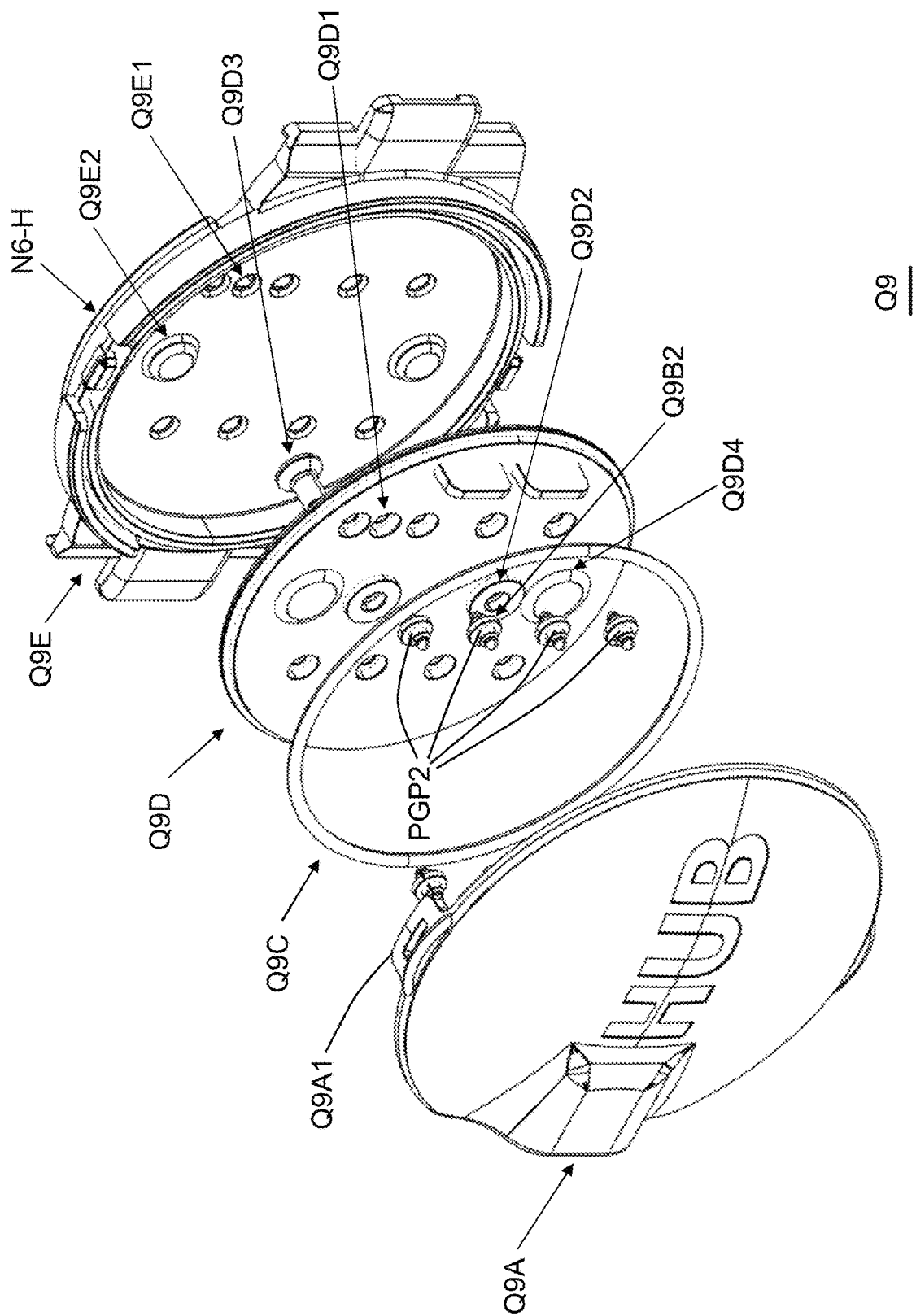
FIG. 10 is a schematic diagram showing another rigid unit according to the preferred embodiment of the present invention.

Please refer to FIG. 10, which is a schematic diagram showing another rigid unit Q9 according to the preferred embodiment of the present invention. Please refer to FIG. 11, which is a schematic diagram showing electrical holes for identifying positions of another rigid unit Q9 according to a preferred embodiment of the present invention. Please refer to FIGS. 10 and 11. For example, the rigid unit Q9 is a signal processing module, which includes a module connector N6-H, a PCB base Q9D, an engaging ring Q9C, a PCB Q9B (not shown) and a protection cover Q9A.

Figure 11:
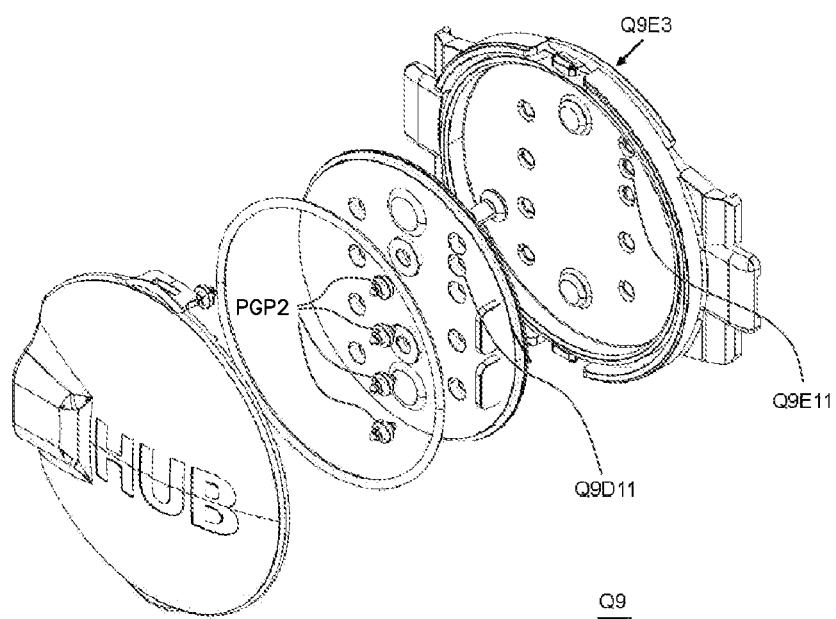
FIG. 11 is a schematic diagram showing electrical holes for identifying positions of another rigid unit according to a preferred embodiment of the present invention.

Please refer to FIGS. 9, 10 and 11. In any one of the aforementioned embodiments, the second wire connecting member N5-H includes the plurality of first electrical contacts N53-H and N54-H. The first bonding structure 24 further includes a rigid unit Q9 having a plurality of second electrical contacts Q9E1, Q9D1, Q9B2, Q9B1 (not shown), Q9E11 and Q9D11 (as shown in FIGS. 10 and 11); and the plurality of fourth electrical contacts Q9E1, Q9D1, Q9B2 and Q9B1 are electrically connected to the plurality of third electrical contacts N53-H and N54-H to electrically connect the rigid unit Q9 to the second wire connecting member N2-H (as shown in FIGS. 9, 10 and 11). At least one of the plurality of fourth electrical contacts Q9E1, Q9D1, Q9B2, Q9B1, Q9E11 and Q9D11 (for example, Q9E11 and Q9D11) is used to form a conduction or a disconnection, wherein the conduction or the disconnection is used to determine a wearing position of the rigid unit Q9.

In FIG. 10, the PCB Q9B (not shown) is fixed to the PCB base Q9D through the PCB base positioning hole Q9B3 (not shown), the PCB base positioning hole Q9D2, the PCB fixing member Q9D3, and the electrical contacts Q9B1 (not shown) and Q9D1; and the engaging ring Q9C is sleeved on the PCB base Q9D, and is then plugged into the module connection base N6-H (i.e., Q9E), so that the PCB base Q9D is fixed in the module connection base N6-H, and then the cover Q9A covers the module connection base N6-H (i.e., Q9E). Please refer to FIGS. 5, 9, 10 and 11. In any one of the aforementioned embodiments, the module connection base Q9E has a curved protrusion structure Q9E3, and the second bonding member N4 also has a curved dike structure N47, which is used to fix the module connection base Q9E to the second bonding member N4. The plurality of third electrical contacts N53-H and N54-H are respectively coupled to the plurality of fourth electrical contacts Q9E1, Q9D1, Q9B2, Q9B1, Q9E11 and Q9D11, such that the rigid unit Q9 is fixed to the second bonding member N4, and the rigid unit Q9 is electrically connected with the signal connecting line P2_2. The stabilization unit NQ9E (not shown) passes through the second bonding member N4 and is locked into an internal screw hole (located on the back of the module connection base Q9E, not shown) of the module connection base Q9E, so that the rigid unit Q9 is directly connected with the second bonding member N4 to mechanically increase the stability of the rigid unit Q9 and avoid loosening. The second bonding structure 24 is combined with the first bonding structure 22 to form the bonding device 20. The signal connecting line P2_2 further includes a signal connector Q1; and the first bonding structure 22 includes a signal connecting hole P1 for being electrically connected to the signal connector Q1.

Figure 5:
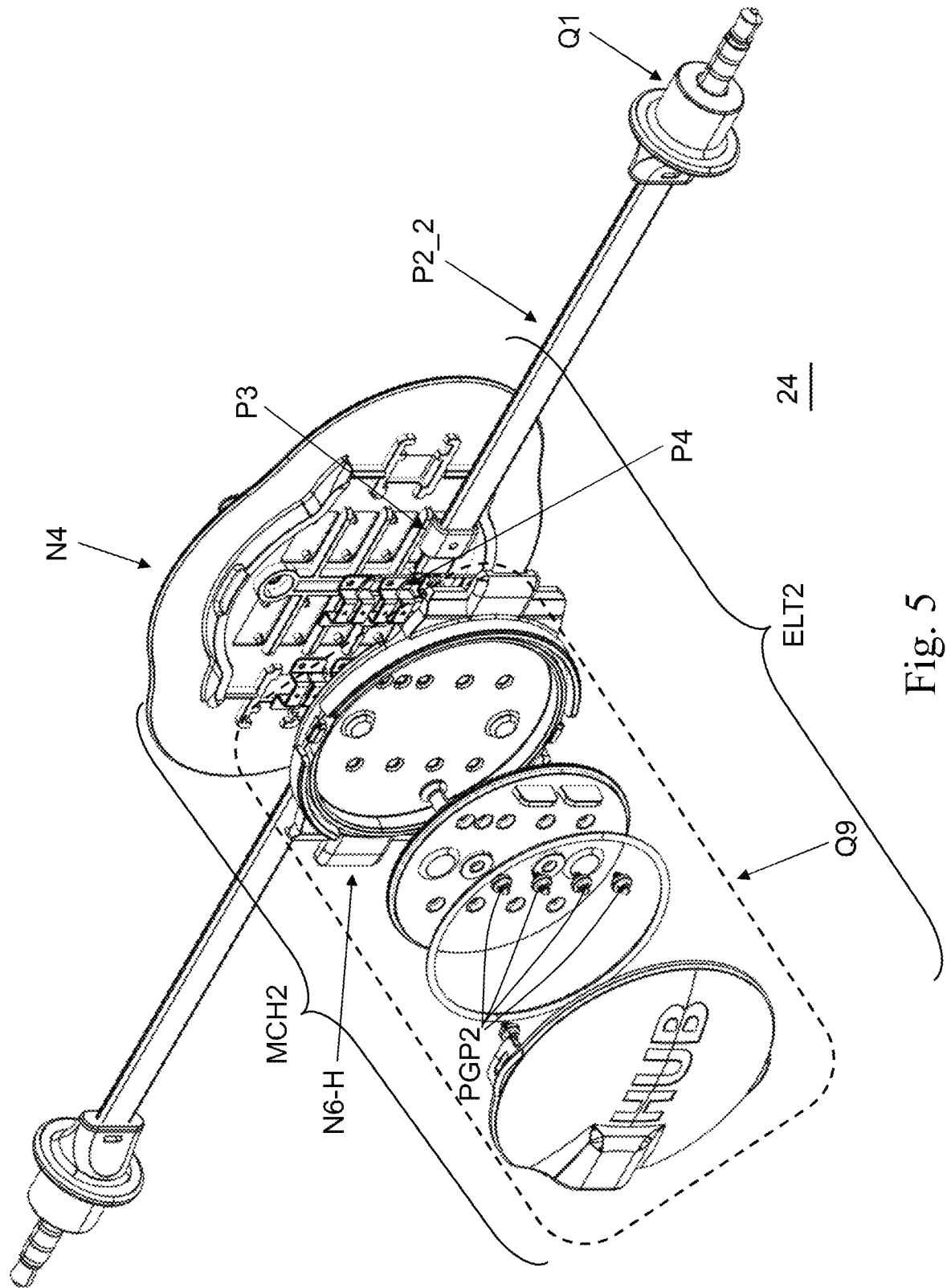
FIG. 5 is a schematic diagram showing a second bonding structure according to a preferred embodiment of the present invention.

In FIG. 5, the second bonding structure 24 further includes a signal line fixing component P3 and another signal connecting line P2_2. The bonding structure 24 includes a plurality of second wires P10 and the signal connector Q1, wherein the plurality of second wires P10 are electrically connected with the plurality of second wires P4 respectively at the signal line fixing component P3.

Figure 12:
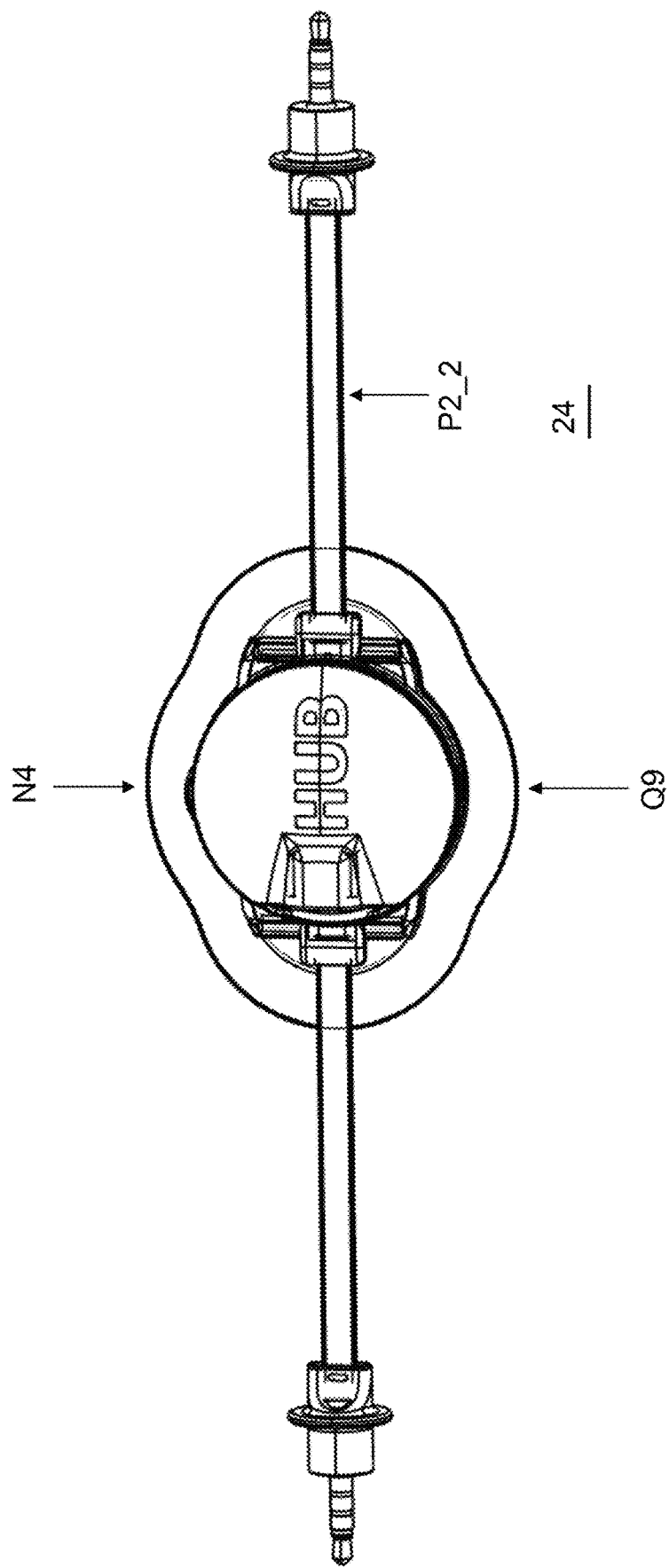
FIG. 12 is a schematic diagram showing a second bonding structure according to another preferred embodiment of the present invention.

Please refer to FIG. 12, which is a schematic diagram showing a second bonding structure 24 according to another preferred embodiment of the present invention. It can be seen in FIGS. 5, 9 and 12 that the second bonding structure 24 includes a rigid unit Q9, such as a signal processing module. The second bonding member N4 and the second wire connecting member N5-H are used to connect and fix the rigid unit Q9 to two signal connecting lines P2_2 by a mechanical bond MCH2 and an electrical bond ELT2. The signal processing module can receive a sensing signal from the sensing module, for example, an (angular) acceleration signal, a (angular) velocity signal and so on, and can transmit it to the data collecting center, and then the data collecting center transmits it to the back-end computer center for analysis. The rigid unit Q9 or P9 may be fixed on an attachment member 21, for example, fabrics or leathers, and then the attachment member 21 is attached on clothes worn by the user USR. The attachment method can be adhesive, sewing for fixedly attaching, or by using a Velcro, zippers, buttons or other detachable fasteners. They are detachably fixed on the attachment member 21 as shown in FIGS. 1A and 1B, and then the attachment member 21 is arranged on the fabric 101 worn on a limb. The rigid unit Q9 or P9 can be detached, so that the fabric 101 can be washed by water like a conventional fabric. In addition, the rigid unit Q9 or P9 can be increased or decreased to be worn on the limbs according to application needs, wherein the rigid unit Q9 can be the signal processing/transmitting module, the device, or the rigid unit P9, i.e., the motion sensing module or device.

Please return to FIGS. 3 and 4, which show another preferred embodiment of the invention for a bonding structure 22 for a wearable device. The bonding structure 22 includes a wire connecting member N2-S, a bonding member N1 and an elastic member P7. In any one of aforementioned embodiments, the wire connecting member N2-S includes a plurality of first connectors N21-S, each of which has a plurality of first mechanical contacts N25-S(holes not shown) and N26-S, and the plurality of first connectors have a plurality of first connecting slots N22-S respectively. The bonding member N1 includes a plurality of second connectors N11, each of which has a plurality of second mechanical contacts N15 (protrusion) and N16 (protrusion). The elastic member P7 has a plurality of first wires P8, wherein the plurality of first wire P8 are correspondingly inserted into (or soldered to) the plurality of first connecting slots N22-S, and thereby are electrically connected to the wire connecting member N2-S. The plurality of first mechanical contacts N25-S (holes not shown) and N26-S(holes) are correspondingly embedded into the plurality of second mechanical contacts N15 (protrusion) and N16 (protrusion), and thereby the plurality of first connectors N21-S are correspondingly embedded into the plurality of second connectors N11 so as to connect with the bonding member N1 mechanically.

Please return to FIGS. 5 and 9, which show another preferred embodiment of the invention for a bonding structure 24 for a wearable device. The bonding structure 24 includes a wire connecting member N5-H, a bonding member N4 and a signal connecting line P2_2. In any one of the aforementioned embodiments, the wire connecting member N5-H includes a plurality of connectors N51-H, each of which has a plurality of first mechanical contacts N55-H (holes not shown) and N56-H (hole), and the plurality of connectors N51-H have a plurality of connecting slots N52-H respectively. The bonding member N4 includes a plurality of second mechanical contacts N45 (protrusion) and N46 (protrusion). The signal connecting line P2_2 has a plurality of first wires P10, electrically connected to the plurality of connecting slots N52-H correspondingly, so as to electrically connect with the wire connecting member N5-H. The plurality of first mechanical contacts N55-H and N56-H are inserted into the plurality of second mechanical contacts N45 and N46 correspondingly, so as to mechanically connect with the bonding member N4.

Please refer to FIGS. 3 and 4 again, which show a node device ND according to a preferred embodiment of the present invention. In any one of the aforementioned embodiments, the node device ND is configured to form a sensing point SN on a signal connecting line P2_1 of a wearable device. The signal connecting line P2_1 has a plurality of signal wires P8, and is used for being connected to a sensing module SM to form the sensing point SN; and the node device SM includes a wearable device body 222, a plurality of first connectors N21-S and a plurality of first electrical contacts N23-S and N24-S. The plurality of first connectors N21-S are disposed on the wearing device body 222. The plurality of first electrical contacts N23-S and N24-S and a plurality of connecting slots N22-S are respectively disposed on the plurality of first connectors N21-S, and electrically connected to the plurality of signal wires P8 to form the node device ND.

In FIG. 4, a signal connecting wire WR is additionally shown according to a preferred embodiment of the present invention. The signal wires WR for the wearable device includes a line base material P7 and a plurality of signal lines P8. The plurality of signal lines P8 are arranged on the line base material P7, wherein each of the plurality of the signal lines P8 has a first part WR1 and a second part WR2. Each first part WR1 forms a sensing node SN for connecting a sensing module SM for forming the sensing node SN, wherein each first part WR1 is a straight line.

Figure 13:
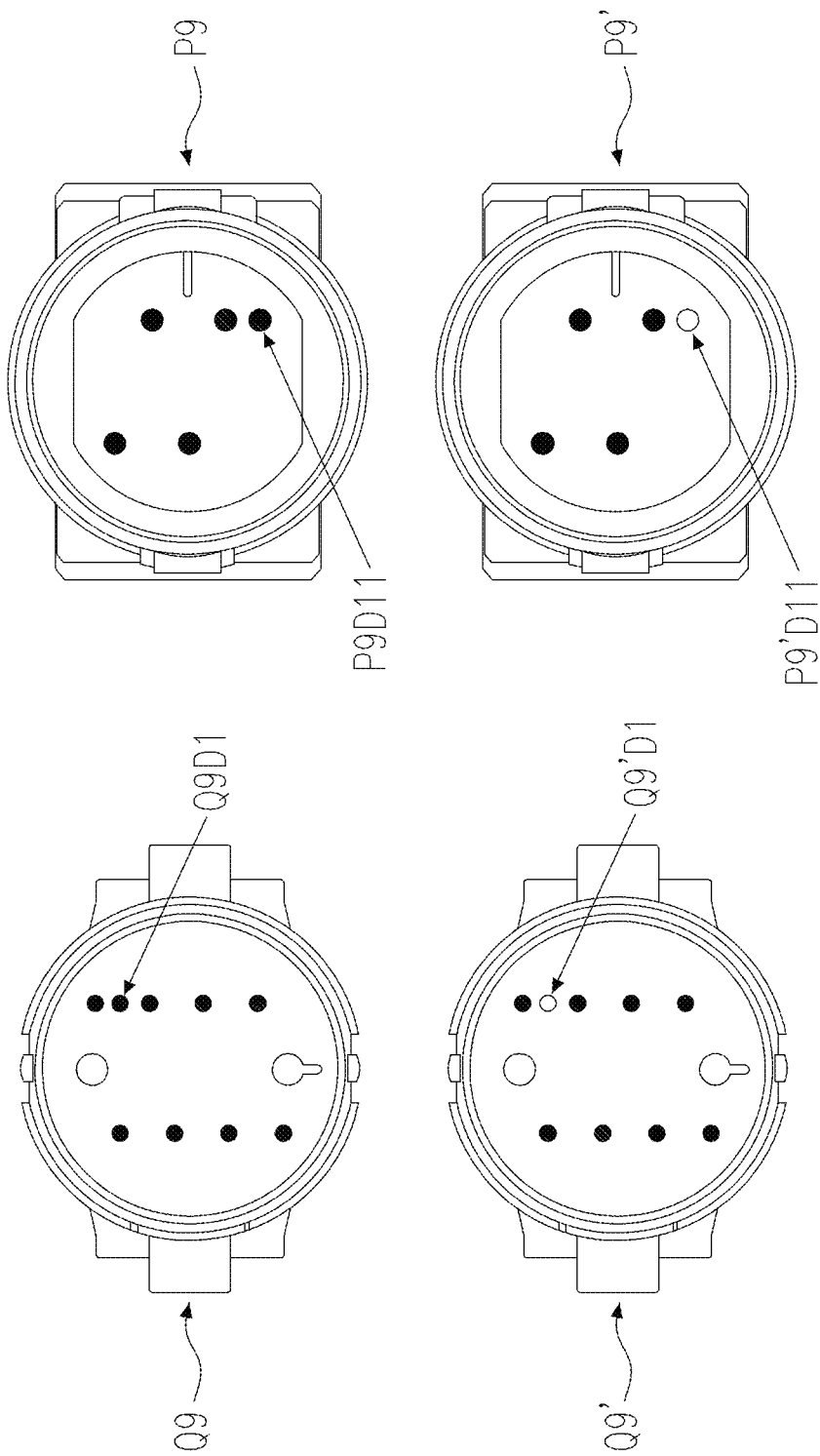
FIG. 13 is a schematic diagram showing the rigid unit used to identify different wearing positions through position indicators according to a preferred embodiment of the present disclosure.

Please refer to FIG. 13, which is a schematic diagram showing the rigid units P9, P9', Q9 and Q9' used to identify different strap positions through position indicators according to a preferred embodiment of the present disclosure. The electrical contact Q9'D1 of the rigid unit Q9' represents that it has been disconnected from the circuit board, which is represented by a hollow circle; and the electrical contact Q9D1 of the rigid unit Q9 represents an electrical conduction with the circuit board, which is represented by a solid circle. This can be used to determine where the rigid units Q9, Q9' are worn on the user's USR. For example, the rigid units Q9, Q9' are signal processing modules. The chest has a wearing position; and when the rigid unit Q9' is worn at the wearing position on the chest, the electrical contact Q9'D1 of rigid unit Q9' is set to be disconnected from the circuit board. The back has a wearing position; and when rigid unit Q9 is worn at the wearing position on the back, the electrical contact Q9D1 of the rigid unit Q9 is set to conduct with the circuit board.

Similarly, the electrical contact P9'D11 of the rigid unit P9' represents that it has been disconnected from the circuit board, which is represented by a hollow circle. The electrical contact P9D11 of the rigid unit P9 represents an electrical conduction with the circuit board, which is represented by a solid circle representation, and thereby the wearing position of the rigid unit (P9, P9') on the user can be determined. For example, the rigid units P9 and P9' are sensing modules. When the rigid unit P9' is worn at the wearing position of the lower limb, the electrical contact P9'D11 of the rigid unit P9' is set to be disconnected from the circuit board. When the rigid unit P9 is worn at the wearing position of the upper limb, the electrical contact P9D11 of the rigid unit P9 is short-circuited to conduct to the circuit board.

When one of the rigid units Q9, Q9' fails, the electrical contact of the other one of the rigid units Q9, Q9' can be changed from conducting to non-conducting (or from non-conducting to conducting), and thus the wearing position attached thereon the malfunction component can be attached with the good one. Similarly, when one of the rigid units P9, P9' fails, the electrical contact of the other one of the rigid units P9, P9' can be set from conductive to non-conductive (or from non-conductive to conductive), and thus the defective component attached on the wearing position can be replaced with a good one to indicate the wearing position. Please refer to FIG. 14, which is a schematic diagram showing the wearable device 30 with the spring connector PGP1 pre-deformed to make electrical connections according to a preferred embodiment of the present disclosure. The spring connector PGP1 is used to combine a protection cover P9A, a module connector P9E and the first bonding member N1 to form a pre-forced combination in a pre-forced manner. Therefore, the pre-forced combination makes the protection cover P9A and the module connector P9E have a corresponding limited displacement in response to the force, that is, a gap, formed by the force, and can achieve the freedom of movement and the detachable combination and separation. When the rigid units Q9 and P9 are worn on the user USR, the effects of the force on these rigid units Q9 and P9 behave the same when the user's limbs are moved or exercised, and these rigid units Q9 and P9 are affected by the forces of the limbs. Taking the rigid unit P9 as an example, that is, the inertial force change between the protection cover P9A and the module connector P9E is caused by the movement of the limbs corresponding to the deformation pre-force of the spring of the spring connector PGP1, so that the gap change between the protection cover P9A and the module connector P9E is limited, and the internal electrical connection formed by the spring connector PGP1 can be maintained stable. Since the detachable combination and separate functions of the protection cover P9A and the module connector P9E can meet the needs of the user USR for disassembling these devices to be used for different parts of the user; as a result, the first coupling structure 22 and the second coupling structure 24 can be detachably combined with the fabric body 101, and can be worn on different parts of the user USR. The elastic member P7 is detachably combined with the fabric body 101, and can be separated from the fabric body 101 to be cleaned. Accordingly, the present disclosure provides a design mechanism and structure that can meet at least the above-mentioned requirements.

Figure 15:
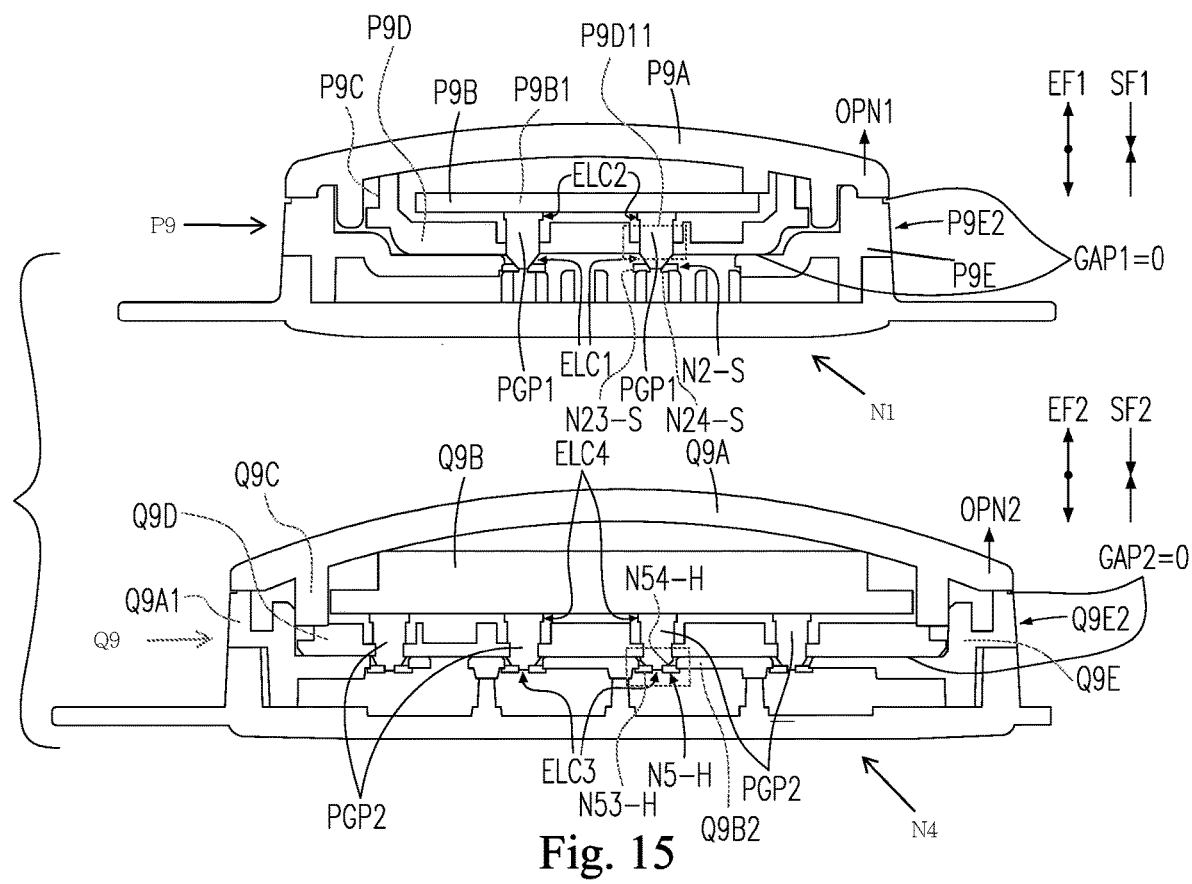
FIG. 15 is a schematic diagram showing a cross-sectional structure of the wearable device according to a preferred embodiment of the present disclosure.

Please refer to FIG. 15, which is a schematic diagram showing the cross-sectional structure of the wearable device 30 according to the preferred embodiment of the disclosure. The wearable device 30 can be a rigid element (P9, Q9), such as a sensing module and/or a signal analysis module.

Figure 16A:
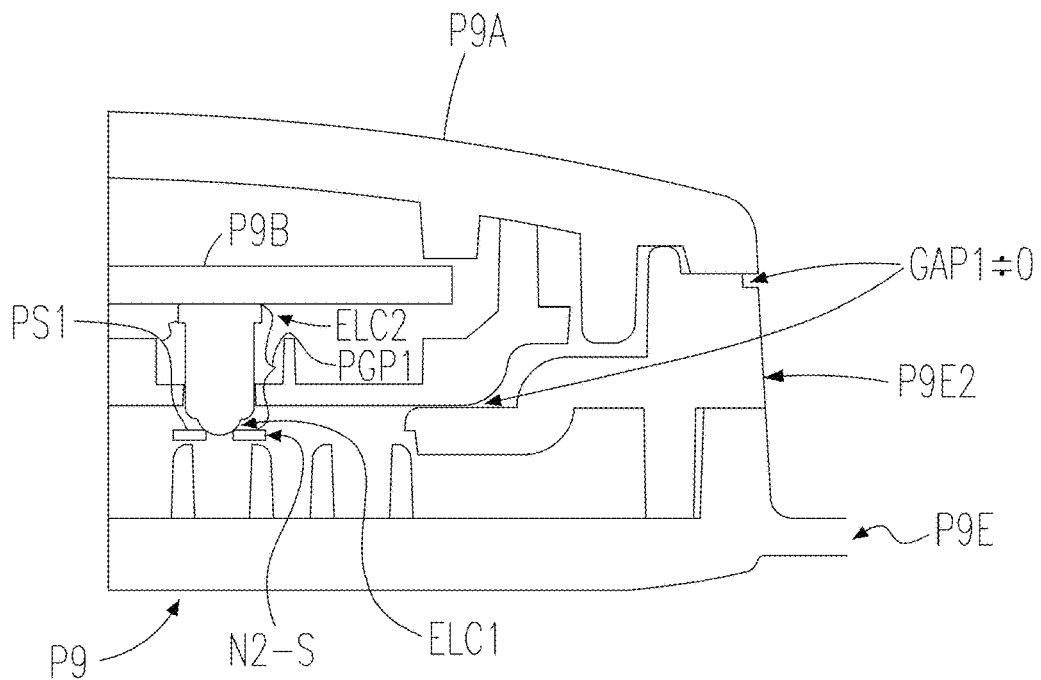
FIGS. 16A and 16B are schematic diagrams showing a cross-sectional structure of a gap being between a protective cover of a sensing module of the wearable device and a module connector according to a preferred embodiment of the present disclosure.
Figure 16B:
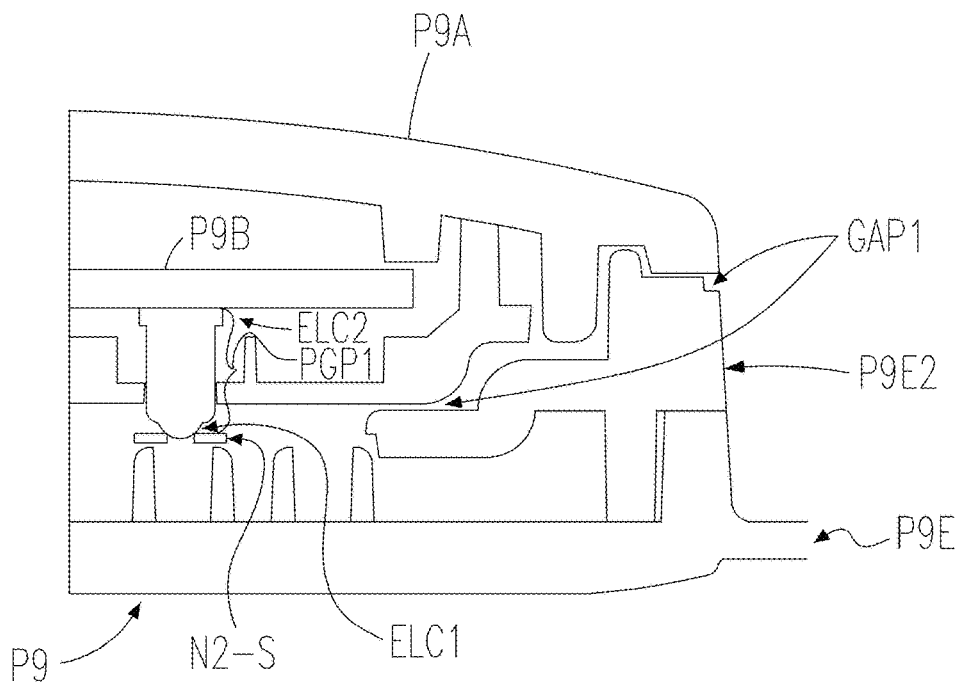

Please refer to FIG. 16A, which is a schematic diagram showing the spring connector maintaining electrical connections, such as ELC1 and ELC2, when the gap GAP1 of the wearable device 30 is close to zero according to the preferred embodiment of the present disclosure. Please refer to FIG. 16B, which is a schematic diagram showing the spring connector maintaining electrical connections, such as ELC1 and ELC2, when the wearable device 30 has a gap, and the gap is not zero according to a preferred embodiment of the present disclosure. The wearable device 30 shown in FIGS. 16A and 16B is an example device of the sensing module. The gap is reserved for being applied by a force through a touching finger or a tool such as a screwdriver, to detachably combining the protection cover P9A with the module connector P9E, and the signal analysis module is also in a similar detachably combining manner. Please refer to FIG. 17, which is a schematic diagram showing a preferred embodiment of the disclosure when the length of the spring connector PGP1 has a variation VR1. Taking the rigid unit P9 shown in FIG. 14 as an example, it can also be applied to another rigid unit Q9. Please refer to FIGS. 3, 4, 6, 7, 14, 15 and 17. The wearable device 30 is used for a user USR to wear for sensing a movement parameter of the user USR, and includes a first bonding structure 22, which has a plurality of first electrical contacts N23-S, N24-S, and a plurality of second electrical contacts P9D11 (referring to FIG. 13) to form correspondingly a plurality of first electrical bonds ELT1, and includes a first module connector P9E, a first wire connecting member N2-S, a first protection cover P9A, a first circuit board P9B and a plurality of first spring connections PGP1. The first module connector P9E has a first tenon structure P9E2. The first wire connecting member N2-S has the plurality of first electrical contacts N23-S, N24-S. The first protection cover P9A is connected to the first module connector P9E via the first tenon structure P9E2, wherein before the first module connector P9E and the first protection cover P9A are connected, a first gap GAP1 is formed therebetween. The first circuit board P9B is fixed on the first protection cover P9A, is arranged between the first module connector P9E and the first protection cover P9A, and has the plurality of second electrical contacts P9D11. The plurality of first spring connectors PGP1 are respectively electrically connected to the plurality of first electrical contacts N23-S, N24-S to form a plurality of first electrical connections ELC1, and are respectively electrically connected to the plurality of second electrical contacts P9D11 to form a plurality of second electrical connections ELC2. In addition, the plurality of first spring connectors PGP1 are arranged between the first module connector P9E and the first circuit board P9B to form a plurality of first pre-deformed PS1, wherein when the user USR has the motion, the plurality of first spring connectors PGP1 ensure, despite the first gap GAP1, that the plurality of the first electrical contacts N23-S, N24-S and the plurality of the second electrical contacts P9D11 keep therebetween the plurality of first electrical bonds ELT1 as shown in FIG. 3.

In some embodiments, the plurality of first spring connectors PGP1 are respectively electrically connected to the plurality of first electrical contacts N23-S, N24-S to form a plurality of first electrical connections ELC1, and are respectively electrically connected to the plurality of second electrical contacts P9D11 to form a plurality of second electrical connections ELC2, and are arranged between the first module connector P9E and the first circuit board P9B to form a plurality of first pre-deformed PS1, wherein: along with the motion of the limb, the first gap GAP1 between the first module connector P9E and the first protection cover P9A has a first variation VR1; and the pre-force of the plurality of first spring connectors PGP1 eliminates the occurrence of the first change VR1 respectively due to the motion, such that the plurality of first electrical contacts N23-S, N24-S and the corresponding plurality of second electrical contacts P9D11 maintain the first electrical bonds ELT1 respectively as shown in FIG. 3.

Accordingly, the wearable device 30 further includes a first bonding member N1, an elastic member P7, and a second bonding structure 24 having a first signal connection line P2_2, wherein: when the first protection cover P9A and the module connector P9E are joined, the first gap GAP1 approaches zero, the plurality of first spring connectors PGP1 are used to maintain a reliability of the first electrical connection ELT1. Each of the plurality of first spring connectors PGP1 is a first compression spring connector. The motion parameter includes at least one of an acceleration parameter, a velocity parameter, and a displacement parameter. The first bonding member N1 is coupled with the first module connector P9E through the first tenon structure P9E2. The elastic member P7 is disposed between the first wire connecting member N2-S and the first bonding member N1.

Figure 14:
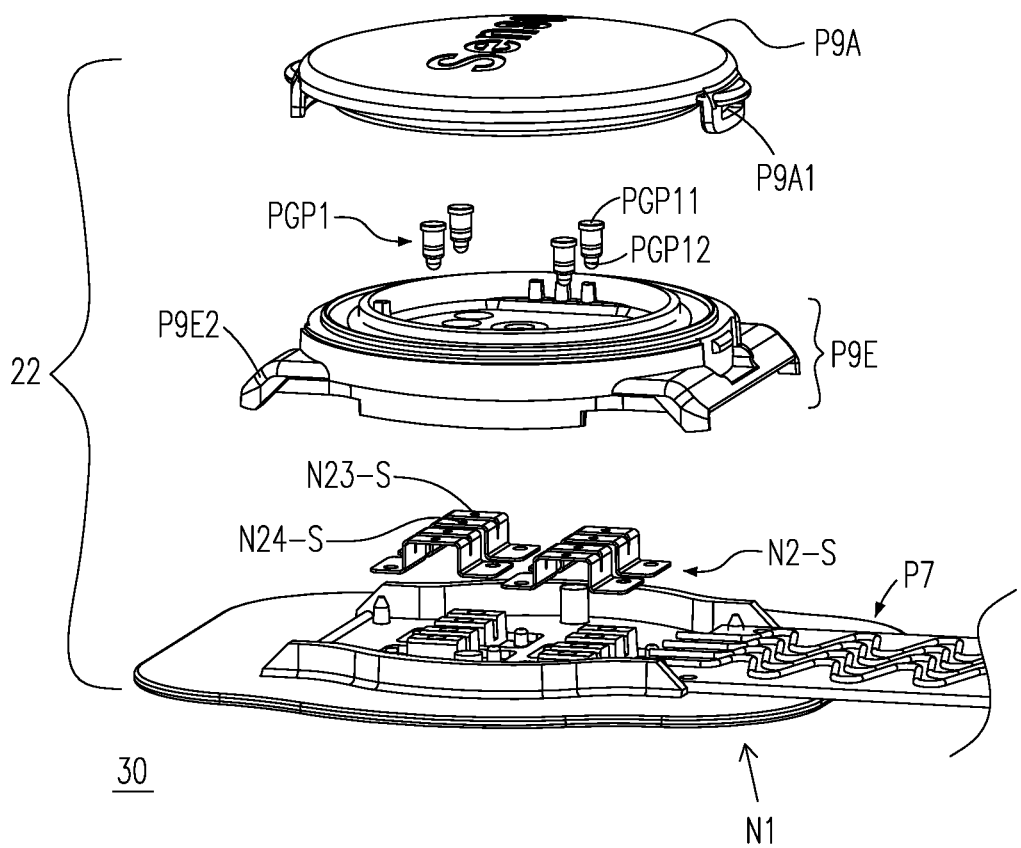
FIG. 14 is a schematic diagram showing the wearable device with a spring connector pre-deformed to perform an electrical connection according to a preferred embodiment of the present disclosure.
Figure 17:
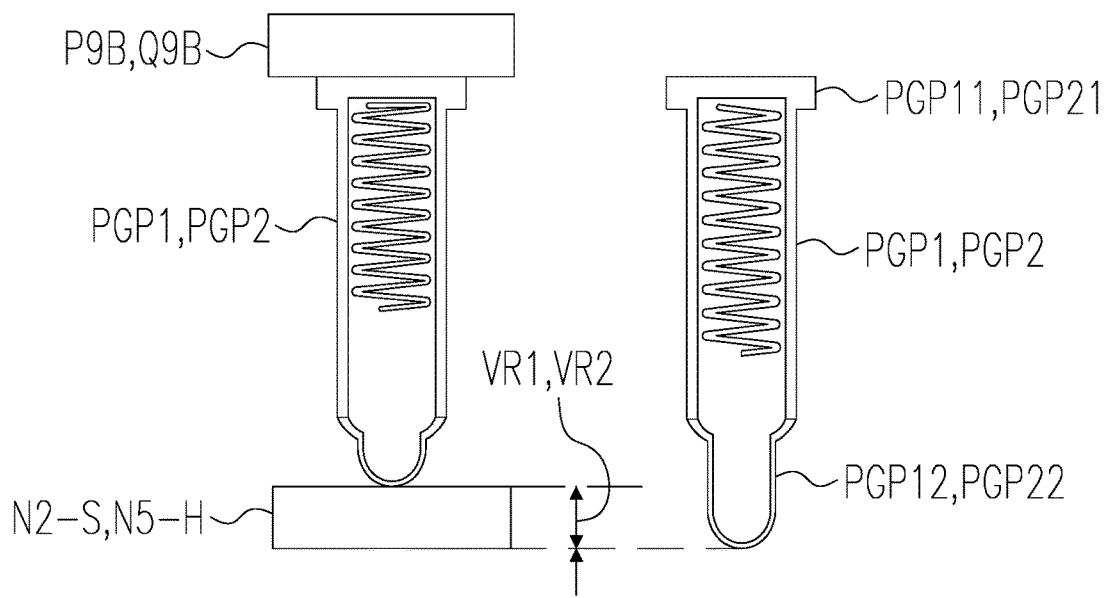
FIG. 17 is a schematic diagram showing that the length of the spring connector is changed according to a preferred embodiment of the present disclosure.

In FIG. 17, each of the plurality of first spring connectors PGP1 includes a first fixing portion PGP11 and a first contact thimble PGP12. The first bonding structure 22 further includes a first rigid unit P9, wherein: the first rigid unit P9 includes the first circuit board P9B and the first protection cover P9A, and has a plurality of second electrical contacts P9B1 disposed on the first circuit board P9B. The plurality of second electrical contacts P9D11 arranged on the module connector P9E, as shown in FIGS. 6 & 7, are aligned with the second electrode contacts P9B1 disposed on the first circuit board P9B, as shown in FIG. 6, and the first fixing portion PGP11 of the plurality of first spring connectors PGP1 contacts the second electrode contacts P9B1 through the plurality of second electrical contacts P9D11, and the first contact thimbles PGP12 of the plurality of first spring connectors PGP1, as shown in FIG. 17, contacts the plurality of first electrical contacts N-23S or N-24S of the first wire connecting member N2-S, as shown in FIG. 14, making the electric connection for the first wire connecting member N2-S and the first circuit board P9B. Each of the plurality of first spring connectors PGP1 is fixed to each of the plurality of second electrical contacts P9D11 respectively. Each of the plurality of first contact thimbles PGP12 passes through and contacts each of the plurality of second electrical contacts P9D11 and each of the plurality of first electrical contacts N23-S, N24-S, so that the first rigid unit P9 is electrically connected to the first wire connecting member N2-S. The first protection cover P9A has a second tenon structure P9A1 to be combined with the first module connector P9E. The first tenon structure P9E2 and the second tenon structure P9A1 are joined to form a first fastening force SF1 between the first protection cover P9A and the first module connector P9E, and the first fastening force SF1 is caused by the deformation of the compression springs of the plurality of the first spring connectors PGP1 as engaging the first protection cover P9A with the first module connector P9E closed. The plurality of first spring connectors PGP1 form the first electrical bonds ELT1 by the first pre-force EF1 between the corresponding plurality of first electrical contacts N23-S, N24-S and the plurality of second electrical contacts P9D11 respectively, wherein the first pre-force EF1 corresponds to the first pre-deformation PS1, and the first pre-force EF1 is a first external expansion force that is opposite to the first fastening force SF1, for example, the elastic force after the compression spring is compressed, and the first external expansion force corresponds to the first fastening force SF1. When the sum of a first opening force OPN1 and the first pre-force EF1 applied to the first protection cover P9A is greater than or equal to the first fastening force SF1, the first protection cover P9A is disassembled; otherwise, the first protection cover P9A and the first module connector P9E are maintained in engagement.

When the user USR moves around or exercises, the movement of the user USR can cause the first protection cover P9A or the first module connector P9E to generate an inertial force, stimulating the existing deformation of the springs on the plurality of first spring connectors PGP1 to change, and cause the first gap GAP1 to generate a variation VR1. For example, when the first protection cover P9A is engaged with the first module connector P9E, the first gap GAP1 approaches zero, and when the rigid unit P9 moves along with the limbs, the variation VR1 of the first gap GAP1 can change. However, since the springs of the plurality of spring connectors PGP1 are in a compressed state at this time, even if the first gap GAP1 is inclining toward enlarging, the springs of the plurality of spring connectors PGP1 still maintain the compressed state to support and maintain electrical bonds.

Please refer to FIGS. 5, 9, 10, 11, 15 and 17. The second bonding structure 24 further includes a second rigid unit Q9. The second rigid unit Q9 includes a second circuit board Q9B and a second protection cover Q9A, and has a plurality of fourth electrical contacts Q9B2 disposed on the second circuit board Q9B. The second bonding structure 24 further includes a plurality of second spring connectors PGP2 and a second module connector Q9E, and the plurality of second spring connectors PGP2 are electrically connected to the corresponding respective third electrical contacts N53-H, N54-H to form a plurality of third electrical connections ELC3, and to electrically connect each of the corresponding plurality of fourth electrical connections Q9B2 to form a plurality of fourth electrical connections ELC4, and are arranged between the second module connector Q9E and the second circuit boards Q9B to form a plurality of second pre-deformed PS2.

There is a second gap GAP2 between the second module connector Q9E and the second protection cover Q9A. When the second protection cover Q9A is engaged with the second module connector Q9E, the second gap GAP2 approaches zero. When the user USR moves around or exercises, this movement of the user USR can cause the second module connector Q9E and the second protection cover Q9A to generate an inertial force, stimulating the existing deformation of the springs on the plurality of second spring connectors PGP2 to change, and making the second gap GAP2 generate a second variation VR2. Similar to the pre-force function of the aforementioned PGP1, the pre-force of the plurality of second spring connectors PGP2 correspondingly eliminates the second variation VR2 that occurs due to the second movement, so that the plurality of third electrical contacts N53-H, N54-H and the plurality of fourth electrical contacts Q9B2 maintain the second electrical bonds ELT2 respectively.

Accordingly, in FIG. 17, each of the plurality of second spring connectors PGP2 includes a second contact thimble PGP22 and a second fixing part PGP21. Each of the plurality of second spring connectors PGP2 is fixed to each of the plurality of fourth electrical contacts Q9B2. Each of the second fixing portions PGP21 and each of the second contact thimble PGP22 are respectively positioned and contact each of the plurality of fourth electrical contacts Q9B2 and the plurality of third electrical contacts N53-H, N54-H, so that the second rigid units Q9 is electrically connected to the second wire connecting member N5-H. The second protection cover Q9A has a fourth tenon structure Q9A1 to be combined with the second module connector Q9E.

Figure 18:
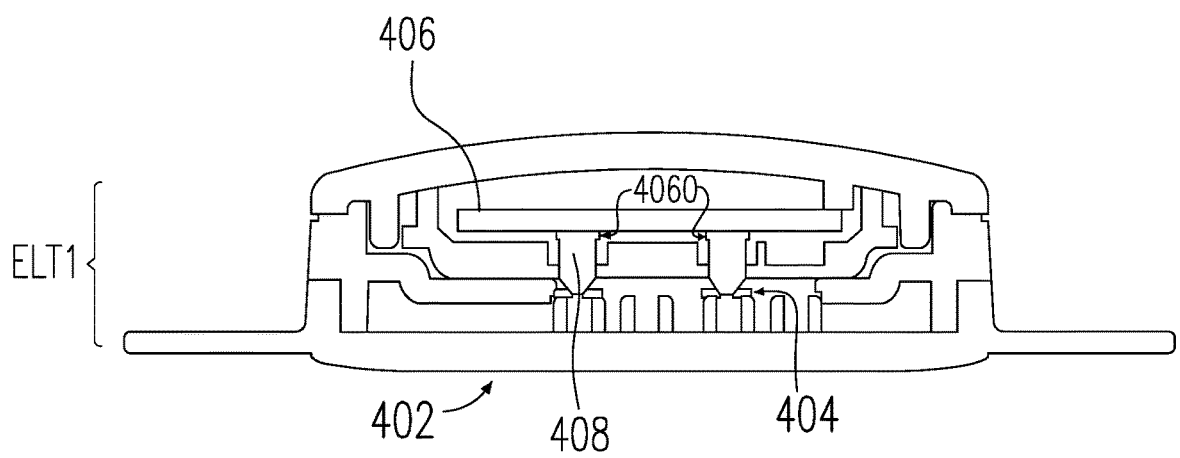
FIG. 18 is a schematic diagram showing a wearable device according to a preferred embodiment of the present disclosure.

Please refer to FIG. 18, which is a schematic diagram showing the wearable device 40 according to a preferred embodiment of the present disclosure. The wearable device 40 is used to be worn by a user USR to sense a motion parameter of the user USR. The wearable device 40 includes a device body 402, a plurality of wires 404, a circuit board 406, and a plurality of spring connectors 408. The plurality of wires 404 are arranged on the device body 402, and are used to transmit a plurality of electrical signals containing the motion parameters. The circuit board 406 is disposed on the device body 402 and has a plurality of second electrical contacts 4060. The plurality of spring connectors 408 are electrically connected between the plurality of second electrical contacts 4060 and the plurality of wires 404 to form a pre-stressed electrical connection therebetween.

The embodiment in FIG. 18 can be combined with any of the foregoing embodiments to form a new embodiment. For example, the plural wires 404 correspond to the plural first wires P8 shown in FIG. 3 and the plural second wires P4 shown in FIG. 4, which are electrically connected to the plural spring connectors 408 respectively through the wire connecting members N2-S, N5-H (that is, the plural spring connectors PGP1, PGP2 in FIGS. 14, 15 and 17). The circuit board 406 corresponds to the circuit board P9B shown in FIG. 6 and the circuit board Q9B shown in FIG. 15, they are electrically connected with the plurality of spring connectors PGP1, PGP2 respectively by the plurality of second electrical contacts 4060, that is, the plurality of second electrical contacts P9B2 shown in FIG. 6, and the plurality of fourth electrical contacts Q9B2 shown in FIG. 10.

Accordingly, the device body 402 includes the module connectors P9E and Q9E, the wire connection members N2-S and N5-H, and the protection covers P9A and Q9A. The module connectors P9E and Q9E have the first tenon structures P9E1 and Q9E1. The wire connecting members N2-S and N5-H have the plural first electrical contacts N23-S, N24-S, N53-H and N54-H respectively. The protection covers P9A and Q9A are connected to the module connectors P9E and Q9E through the first tenon structures P9E1 and Q9E1. The plurality of spring connectors PGP1, PGP2 are electrically connected to the corresponding plurality of first electrical contacts N23-S, N24-S to form a plurality of first electrical connections ELC1, ELC3, and are electrically connected to the corresponding plurality of second electrical contacts P9B2, Q9B2 to form a plurality of second electrical connections ELC2, ELC4, and are arranged between the wire connecting member (N2-S, N5-H) and the circuit board (P9B, Q9B) to form a plurality of first pre-deformations PS1, PS2. There are a first gap GAP1 and a second gap GAP2 between the module connectors P9E, Q9E and the protection covers P9A, Q9A, respectively. When the protection covers P9A, Q9A and the module connectors P9E, Q9E are joined, the first gap GAP1 and the second gap GAP2 respectively approach zero. Due to the movement or exercise of the user USR, the inertial force occurs between the module connectors P9E, Q9E and the protection covers P9A, Q9A, stimulating the springs on the plurality of first spring connectors PGP1 and the plurality of second spring connectors PGP2 to change the existing deformation, so as to produce a first variation VR1 of the first gap GAP1 and a second variation VR2 of the second gap GAP2 respectively. The individual pre-forces of the plurality of spring connectors PGP1 and PGP2 correspondingly eliminate the first variation VR1 and the second variation VR2 that occur due to the movement, so that the corresponding plurality of first electrical contacts N23-S, N24-S, N53-H, N54-H and the corresponding plurality of second electrical contacts P9B2, Q9B2 maintain a first electrical bond ELT1 and a second electrical bond ELT2 respectively.

The plurality of spring connectors PGP1 and PGP2 are used to maintain the reliability of the first electrical bond ELT1 and the second electrical bond ELT2. Each of the plural spring connectors PGP1, PGP2 is a compression spring connector. Each of the plurality of spring connectors PGP1, PGP2 includes a contact thimble (PGP12, PGP22) and a fixing part (PGP11, PGP21). Each of the fixing parts PGP11, PGP21 and each of the contact thimbles PGP12, PGP22 pass through and contact the plurality of second electrical contacts P9B2, Q9B2 and the plurality of first electrical contacts N23-S, N24-S, N53-H, N54-H, so that the rigid unit is electrically connected to the wire connecting members N2-S, N5-H. The protection cover (P9A, Q9A) has a second tenon structure (P9A1, Q9A1) to be combined with the module connector (P9E, Q9E). The first tenon (or locking) structure (P9E1, Q9E1) and the second tenon (or locking) structure (P9A1, Q9A1) are joined to form a first fastening force (SF1, SF2) between the protection cover (P9A, Q9A) and the module connector (P9E, Q9E). The plurality of spring connectors PGP1, PGP2 form the first electrical bond ELT1 and the second electrical bond ELT2 between the plurality of first electrical contacts N23-S, N24-S, N53-H, N54-H and the plurality of second electrical contacts P9B2, Q9B2 by the pre-forces EF1, EF2, wherein the first pre-force (EF1, EF2) corresponds to the first pre-deformation (PS1, PS2), the first pre-force (EF1, EF2) is a first outward force in reversed to the first fastening force (SF1, SF2). When the sum of the first pre-force (EF1, EF2) and a first opening force (OPN1, OPN2) applied to the protection cover (P9A, Q9A) is greater than or equal to the first fastening force (SF1, SF2), the protection cover (P9A, Q9A) is disassembled, otherwise the protection cover (P9A, Q9A) and the module connector (P9E, Q9E) remain engaged.

The motion parameter includes at least one of an acceleration parameter, a velocity parameter, and a displacement parameter. The device body 402 is attached to a fabric body 101 by an elastic member P7. The elastic member P7 is attached to the fabric body 101 by at least one of a Velcro, a zipper, a sewing material and an adhesive substance. The device body 402 is detachably combined with the fabric body 101, and can be worn on different parts of the user USR. The elastic member P7 is detachably combined with the fabric body 101, and can be separated from the fabric body 101 for clean.

While the invention has been described in terms of what is presently considered to be the most practical and preferred embodiments, it is to be understood that the invention need not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:
1. A wearable device for sensing a motion parameter of a user having a motion, comprising:

a first bonding structure having a plurality of first electrical contacts and a plurality of second electrical contacts to form correspondingly a plurality of first electrical bonds, and including:
  a first module connector having a first tenon structure;
  a first wire connecting member having the plurality of first electrical contacts;
  a first protection cover connected to the first module connector via the first tenon structure, wherein before the first module connector and the first protection cover are connected, there is formed therebetween a first gap;
  a first circuit board fixed on the first protection cover, configured between the first module connector and the first protection cover, and having the plurality of second electrical contacts; and
  a plurality of first spring connectors respectively electrically connected between the plurality of first and second electrical contacts to form a plurality of first and a plurality of second electrical connections respectively, and configured between the first module connector and the first circuit board to form a plurality of first pre-deformations, wherein when the user has the motion, the plurality of first spring connectors ensure, despite the first gap, that the pluralities of the first and second electrical contacts keep therebetween the plurality of first electrical bonds.

2. The wearable device as claimed in claim 1, wherein the wearable device further includes:
  a first bonding member;
  an elastic member; and
  a second bonding structure having a first signal connection line, wherein:
  the first gap approaches to zero when the first protection cover and the module connector are joined together;
  the plurality of first spring connectors are configured to keep a reliability of the plurality of first electrical bonds; and
  each of the plurality of first spring connectors is a first compression spring connector.

3. The wearable device as claimed in claim 2, wherein:
  the motion parameter includes at least one of an acceleration parameter, a velocity parameter and a displacement parameter;
  the first bonding member connects with the first module connector through the first tenon structure;
  the elastic member is disposed between the first wire connecting member and the first bonding member;
  the first bonding structure has a plurality of first mechanical structures;
  the first wire connecting member, the first bonding member, and the elastic member form a first mechanical bond through the plurality of first mechanical structures correspondingly;
  the first wire connecting member, the first bonding member, and the elastic member form the first electrical bond through the plurality of first electrical contacts correspondingly; and
  the elastic member is electrically connected to the first signal connecting line to combine the first bonding structure with the second bonding structure together.

4. The wearable device as claimed in claim 2, wherein:
  the second bonding structure further includes a plurality of second mechanical structures and a plurality of third electrical contacts to form a second mechanical bond and a second electrical bond correspondingly;
  the first wire connecting member includes a plurality of first connectors, each of which has a first connecting slots-;
  the first bonding member includes a plurality of second connectors, each second connector corresponds to the respective first connector;
  the elastic member has a plurality of first flexible wires;
  the plurality of first flexible wires are correspondingly inserted into the plurality of first connecting slots to electrically connect the first wire connecting member;
  the elastic member is an elastic fabric member, and further includes a plurality of elastic fabrics, each of which is attached to a plurality of first wires;
  any two adjacent ones of the plurality of first wires have a same space therebetween and each first wire has a configured shape, wherein the configured shape is a wave shape; and
  each first connector is a conductor connector, and each second connector is an isolator.

5. The wearable device as claimed in claim 4, wherein:
  each first connector has a concave portion and the plurality of first electrical contacts located at a bottom of the concave portion, and each second connector has a protruding portion, an upper connector hole and a lower connector hole located at a top of the corresponding protruding portion; and
  each protruding portion is inserted into the corresponding concave portion, and the plurality of first electrical contacts are respectively mechanically connected to the upper connector hole and the lower connector hole such that the plurality of first connectors and the plurality of second connectors are respectively connected mechanically.

6. The wearable device as claimed in claim 4, wherein:
  the wearable device is attached to a fabric body by the elastic member;
  the elastic member is attached to the fabric body by a Velcro, a zipper, a sewing material, or an adhesive substance;
  the first bonding structure is worn on an active portion of the user, and the active portion includes a limb, a head, a neck, a torso or hips;
  the user generates the motion during an activity;
  the first bonding structure is detachably combined with the fabric body and is worn on different parts of the user;
  the elastic member is detachably combined with the fabric body, and is separated from the fabric body for cleaning;
  the first bonding structure further comprises:
  a signal line fixing component; and
  a second signal connecting line including a plurality of second wires and a signal connecting hole, wherein the plurality of first wires are electrically connected to the plurality of second wires respectively at the signal line fixing component; and
  the first bonding structure is combined with the second bonding structure to form a bonding device, wherein the second bonding structure includes a signal connector electrically connected to the signal connecting hole.

7. The wearable device as claimed in claim 6, wherein:
  the second bonding structure further includes a second wire connecting member having a plurality of third connectors, each third connector hasp a hird connecting slot and a plurality of third mechanical contacts, and the second bonding structure further includes a second bonding member including a plurality of fourth mechanical contacts;

the plurality of second wires are respectively inserted into the plurality of third connecting slots to be electrically connected to the second wire connecting member;

the plurality of third mechanical contacts are respectively inserted into the plurality of fourth mechanical contacts to be mechanically connected to the second bonding member;

the second bonding structure is detachably attached to a relatively stable portion of a user, and the relatively stable portion includes a shoulder, a chest, a back or a waist;

the second bonding member further includes a plurality of positioning protrusions;

the plurality of third connectors are configured to be mechanically connected to the second bonding member according to the plurality of positioning protrusions;

each third connector is a conductor connector, and the plurality of positioning protrusions are respectively a plurality of insulator portions;

the plurality of third mechanical contacts include a plurality of via holes, and the plurality of fourth mechanical contacts respectively penetrate the plurality of via holes to be mechanically connected to the plurality of third connectors; and each of the third connectors further has a recess and the plurality of third electrical contacts located at the bottom of the recess.

8. The wearable device as claimed in claim 1, wherein:
each of the first spring connectors includes a first pogo-pin and a first fix portion;

the first bonding structure further comprises a rigid unit, wherein the first rigid unit includes the first circuit board and the first protection cover, and has the plurality of second electrical contacts configured on the first circuit board, the plurality of first spring connectors are electrically connected to the plurality of second electrical contacts respectively, and the plurality of first pogo-pins are positioned to respectively contact the plurality of second electrical contacts and the plurality of the first electrical contacts to cause the first rigid unit to be electrically connected to the first wire connecting member;

the first protection cover has a second tenon structure for connecting with the first module connector;

the first tenon structure and the second tenon structure are combined together to produce a first fastening force between the first protection cover and the first module connector;

the plurality of first spring connectors respectively form the first and second electrical connections with the plurality of first electrical contacts and the plurality of second electrical contacts correspondingly by a first pre-force, wherein the first pre-force forms the first pre-deformation, and the first pre-force is a first external expansion force acting against the first fastening force;

when a first opening force applied to the first protection cover is greater than or equal to a difference between the first fastening force and the first pre-force, the first protection cover is disassembled; and if not, the first protection cover remains in engagement with the first module connector;

at least one of the plurality of second electrical contacts is used to form a conduction or a disconnection, wherein the conduction or the disconnection is used to determine a wearing position of the first rigid unit;

the first rigid unit is a motion sensing module; and each of the plurality of second connectors further includes a plurality of holes, wherein the plurality of first electrical contacts are respectively coupled to the plurality of holes and the plurality of second electrical contacts such that the first rigid unit is fixed on the first bonding member.

9. The wearable device as claimed in claim 1, wherein:
the second bonding structure further includes a second rigid unit;

the second rigid unit includes a second circuit board and a second protection cover, and has a plurality of fourth electrical contacts disposed on the second circuit board;

the second bonding structure further includes a plurality of second spring connectors and a second module connector, and the plurality of second spring connectors are electrically connected to the plurality of third electrical contacts respectively to form a plurality of third electrical connections, the plurality of second spring connectors are electrically connected to the plurality of fourth electrical contacts respectively to form a plurality of fourth electrical connections, and the plurality of second spring connectors are arranged between the second module connector and the second circuit boards to form a plurality of second compression pre-deformations;

there is a second gap between the second module connector and the second protection cover;

when the second protection cover is combined with the second module connector, the second gap approaches zero;

the plurality of second spring connectors ensures, despite of the second gap, when the user has a second movement, the plurality of third electrical contacts and the plurality of fourth electrical contacts respectively maintain therebetween a plurality of electrical connections;

each of the plurality of second spring connectors includes a second contact thimble and a second fixing part;

each of the plurality of second spring connectors is in electrical contact with a respective one of the plurality of fourth electrical contacts;

each of the second contact thimbles is positioned to contact a respective one of the plurality of fourth electrical contacts and a respective one of the plurality of third electrical contacts so that the second rigid unit is electrically connected to the second wire connecting member;

the second protection cover has a fourth tenon structure to be combined with the second module connector;

at least one of the plurality of fourth electrical contacts is used to form a conduction or a disconnection, wherein the conduction or the disconnection is used to determine a wearing position of the second rigid unit;

the second rigid unit is a signal processing module;

the second bonding structure is combined with the first bonding structure to form the wearable device; and the first signal connecting line further includes a signal connector, and the first bonding structure includes a signal connecting hole for being electrically connected to the first signal connector.

10. A wearable device for sensing a motion parameter of a user, comprising:
a module connector;
a wire connecting member having a plurality of first electrical contacts;

a first protection cover connecting thereto the module connector;

a circuit board having a plurality of second electrical contacts corresponding to the plurality of the first electrical contacts; and a plurality of spring connectors electrically connected to the plurality of first electrical contacts and the plurality of second electrical contacts correspondingly to form a plurality of first electrical connections and a plurality of second electrical connections respectively, and configured between the wire connecting member and the first circuit board to form a plurality of first pre-deformations.

11. The wearable device as claimed in claim 10, wherein:
the module connector and the protection cover form therebetween a first gap;
when the protection cover is combined with the module connector, the first gap approaches zero;
the plurality of spring connectors ensures, despite of the first gap, when there is a vibration, the plurality of first electrical contacts and the plurality of second electrical contacts maintain a plurality of first electrical connections;
the wearable device further includes a bonding structure including:
 a bonding member including a plurality of second connectors, each second connector having a plurality of second mechanism contacts; and
 an elastic member having a plurality of first wires;
the wire connecting member includes a plurality of first connectors, wherein each first connector has a plurality of first mechanical contacts and a plurality of first electrical contacts, and has a plurality of first connecting slots corresponding to the plurality of first connectors; and
the circuit board is fixed on the protection cover and arranged between the module connector and the protection cover.

12. The wearable device as claimed in claim 11, wherein:
the bonding structure further includes a module connector having a first tenon structure, and the bonding member bonds to the module connector through the first tenon structure;
the plurality of first wires are respectively inserted into the plurality of first connector slots to be electrically connected to the wire connecting member;
the plurality of first mechanical contacts are respectively inserted into the plurality of second mechanical contacts such that the plurality of first connectors are respectively inserted into the plurality of second connectors to be mechanically connected to the bonding member;
the bonding structure can be fixedly or detachably worn on an active part of a user, and the active part includes a limb, head, neck, trunk, hip or foot; and
the elastic member is an elastic fabric member and includes a plurality of elastic fabrics and the plurality of first wires, and each of the elastic fabrics is coupled to the plurality of first wires, wherein the plurality of first wires are arranged in a form that does not intersect with one another, and each of the plurality of first wires is wavy and flexible.

13. The wearable device as claimed in claim 11, wherein:
each of the first connectors is a conduct connector, and each of the second connectors is an insulation connector;

the bonding structure has a plurality of second connector slots corresponding to the plurality of second connectors;
the plurality of first wires are respectively inserted into the plurality of second connectors to form a mechanical connection to the bonding member;
the plurality of first mechanical contacts include a plurality of via holes, and the plurality of second mechanical contacts include a plurality of protrusions respectively inserted into the plurality of via holes to be connected with the plurality of first connectors;
each of the plurality of first connectors has a concave portion and the plurality of first electrical contacts located at a bottom of the concave portion, and each of the plurality of second connectors has a protruding portion, an upper connector hole and a lower connector hole located at a top of the corresponding protruding portion; and
each of the plurality of protruding portions is inserted into the respective concave portion, and the plurality of first electrical contacts are mechanically connected to the upper connector hole and the lower connector hole such that the plurality of first connectors and the plurality of second connectors are respectively connected mechanically.

14. The wearable device as claimed in claim 11, wherein:
each of the plurality of spring connectors includes a contact thimble and a fixing part;
the bonding structure further includes a rigid unit, wherein:
 the rigid unit includes the circuit board and the protection cover, and has the plurality of second electrical contacts disposed on the circuit board;
 each of the plurality of spring connectors is electrically connected with a respective one of the plurality of second electrical contacts; and
 each contact thimble is positioned to contact a respective one of the plurality of second electrical contacts and a respective one of the plurality of first electrical contacts so that the rigid unit is electrically connected to the wire connecting member; and
the protection cover has a second tenon structure to be combined with the module connector.

15. The wearable device as claimed in claim 14, wherein:
the first tenon structure and the second tenon structure are joined to cause a first fastening force to form between the protection cover and the module connector;
the plurality of spring connectors form the first electrical connections and the second electrical connections between the plurality of first electrical contacts and the plurality of second electrical contacts by a first pre-force, wherein the first pre-force forms the first pre-deformation, and the first pre-force is a first external expansion force acting against the first fastening force;
when a sum of a first opening force and the first pre-force applied to the protection cover is greater than or equal to the first fastening force, the protection cover is disassembled; and if not, the protection cover and the module connector remain joined; and
at least one of the plurality of second electrical contacts is used to form a conduction or a disconnection, wherein the conduction or the disconnection is used to determine a wearing position of the rigid unit.

16. The wearable device as claimed in claim 11, wherein:
the rigid unit is a motion sensing module or a processing module; and each of the plurality of second connectors further includes a plurality of holes, wherein the plurality of first electrical contacts are respectively coupled to the plurality of holes and the plurality of second electrical contacts such that the rigid unit is fixed to the bonding member;

the bonding structure further comprises:

a signal line fixing component; and a second signal connecting line including a plurality of second wires and a signal connecting hole, wherein the plurality of first wires are electrically connected to the plurality of second wires respectively at the signal line fixing component; and the bonding structure is combined with another bonding structure to form the bonding device, wherein the another bonding structure includes a signal connector electrically connected to the signal connecting hole.

17. A wearable device for a user for sensing a motion parameter of the user, including:

a device body having plural first electrical contacts;

a plurality of wires disposed on the device body for conducting a plurality of electrical signals reflecting the motion parameter;

a circuit board disposed on the device body and having a plurality of second electrical contacts; and a plurality of spring connectors electrically connected between the plurality of second electrical contacts and the plurality of wires respectively to form a pre-stressed electrical connection therebetween.

18. The wearable device as claimed in claim 17, wherein:

the device body includes:

a module connector having a first tenon structure;

a wire connecting member having the plural first electrical contacts; and a protection cover connected to the module connector by the first tenon structure;

the plurality of spring connectors are electrically connected to the plurality of first electrical contacts respectively to form a plurality of first electrical connections, and are electrically connected to the plurality of second electrical contacts respectively to form a plurality of second electrical connections, and arranged between the wire connecting member and the circuit board to form a plurality of first pre-deformations;

there is a first gap between the module connector and the protection cover;

when the protection cover is combined with the module connector, the first gap approaches zero;

the plurality of spring connectors ensure, despite the first gap, when there is a vibration, the plurality of first electrical contacts and the plurality of second electrical contacts maintain a first electrical connection;

the device body further includes a bonding structure, and the bonding structure includes:

a bonding member including a plurality of second connectors, each of which has a plurality of second mechanical contacts; and an elastic member having a plurality of first wires;

the wire connecting member includes a plurality of first connectors, wherein each of the first connectors has a plurality of first mechanical contacts and a plurality of first electrical contacts, and has a plurality of first connector slots corresponding to the plurality of first connectors;

the circuit board is fixed on the protection cover and disposed between the module connector and the protection cover;

the bonding structure further includes a module connector having a first tenon structure, and the bonding member is combined with the module connector by the first tenon structure;

the plurality of spring connectors are used to maintain a reliability of the first electrical connections; and each of the plurality of spring connectors is a compression spring connector.

19. The wearable device as claimed in claim 18, wherein:

each of the plurality of spring connectors includes a contact thimble and a fixing part;

the bonding structure further includes a rigid unit, wherein:

the rigid unit includes the circuit board and the protection cover, and has the plurality of second electrical contacts disposed on the circuit board;

each of the plurality of spring connectors is electrically connected with a respective one of the plurality of second electrical contacts;

each contact thimble is positioned to contact a respective one of the plurality of second electrical contacts and a respective one of the plurality of first electrical contacts so that the rigid unit is electrically connected to the wire connecting member;

the protection cover has a second tenon structure to be combined with the module connector;

the first tenon structure and the second tenon structure are joined to form a first fastening force between the protection cover and the module connector;

the plurality of spring connectors form the first and second electrical connections between the plurality of first electrical contacts and the plurality of second electrical contacts by a first pre-force, wherein the first pre-force forms the first pre-deformations, and the first pre-force is a first external expansion force acting against the first fastening force;

when a sum of a first opening force and the first pre-force applied to the protection cover is greater than or equal to the first fastening force, the protection cover is disassembled; and if not, the protection cover and the module connector remain joined;

the rigid unit has a plurality of second electrical contacts electrically connected to the plurality of first electrical contacts so that the rigid unit is electrically connected to the wire connecting member;

at least one of the plurality of second electrical contacts is used to form a conduction or a disconnection, wherein the conduction or the disconnection is used to determine a wearing position of the rigid unit;

the rigid unit is a motion sensing module or a processing module; and the bonding structure is combined with another bonding structure to form a bonding device, wherein the another bonding structure includes a signal connector electrically connected to a signal connecting hole.

20. The wearable device as claimed in claim 17, wherein:

the device body is attached to a fabric body by an elastic member;

the elastic member is attached to the fabric body by a Velcro, a zipper, a sewing material, or an adhesive substance;

the wearing device is worn on an active part of a user, and the active part includes a limb, head, neck, torso, and hip;

the device body is detachably combined with the fabric body and is worn on different parts of the user; and the elastic member is detachably combined with the fabric body, and is separated from the fabric body for cleaning.

* * * * *